US005989189A

United States Patent [19]
LeBlanc et al.

[11] Patent Number: 5,989,189
[45] Date of Patent: Nov. 23, 1999

[54] OPHTHALMIC ULTRASOUND IMAGING

[75] Inventors: Paul D. LeBlanc, Greenbush; Neils E. Andersen, Stoughton, both of Mass.

[73] Assignee: Mentor Corporation, Santa Barbara, Calif.

[21] Appl. No.: 08/956,698

[22] Filed: Oct. 24, 1997

[51] Int. Cl.[6] .................................................. A61B 8/00
[52] U.S. Cl. ......................................... 600/437; 600/443
[58] Field of Search ................................... 600/437, 443, 600/447; 128/916

[56] References Cited

PUBLICATIONS

Diaz, Gonzalo E., "Ultrasound Color Imaging," World Wide Web pages at http://www.wp.com/ultrasound, Nov. 2, 1996.
Mentor Ophthalmics, Inc. "The Advent™ of Imaging: Technology for the Total Eye," May, 1996.

Primary Examiner—Marvin M. Lateef
Assistant Examiner—Maulin Patel
Attorney, Agent, or Firm—Fish & Richardson P.C.

[57] ABSTRACT

A system for producing visual representation of eye structures that includes an ultrasonic transducer, a processor, and a display device. The processor translates electronic signals received by the transducer into image data for display by correlating echo intensities with multichromatic color hues. The processor can also translate the electronic signals by correlating the echo signal intensities with display characteristics, such as brightness, by using gamma curves that have at least one portion that is substantially continuous and non-monotonic. The processor can also translate the electronic signals into an image that shows different characteristics of the electronic signals in different display characteristics (i.e. one characteristic is color coded while another characteristic affects how brightly a color appears). The processor can also process phase information to both emphasize the depiction of eye structure boundaries and aid in distinguishing reverberation echo signals from genuine ones. The processor can also process time persistence information and thus create images where moving eye structures appear brighter or dimmer than stationary eye structures.

36 Claims, 24 Drawing Sheets

— RED
······ GREEN
—·— BLUE
—··— GRAY

OPHTHALMIC ULTRASOUND IMAGING

The file of this patent contains color photographs. Copies of this patent with color photographs will be provided by the Patent and Trademark Office upon request and payment of the necessary fee.

REFERENCE TO APPENDICES

Text appendix A and color printout appendix B are being submitted with the present application.

BACKGROUND OF THE INVENTION

The present invention relates to ultrasound imaging systems that produce images of eye structures.

Ultrasound has provided physicians, ophthalmologists, and others the ability to examine eye structures without invasive surgery. An ultrasound transducer sends an ultrasound signal into an eye (and possibly surrounding tissue as well) and "listens" for signal echoes. A signal echo indicates the location of a change in impedance (a function of material density and stiffness) within the eye structures. The intensity of the echo signal indicates the amount of the change in impedance. The ultrasound signals detect not only typical eye structures such as the cornea, retina, sclera, etc., but also aberrations such as tumors and blood trapped within an eye's vitreous.

A known version of the Mentor Ophthalmics Advent A/B™ System processes ultrasound signals to create images of eye structures by displaying the different ultrasound signal intensities in one of 256 shades of grey. Since the human eye has some difficulty in differentiating close shades of grey, the Advent A/B™ System provides operators with tools to alter the image to prevent display limitations from impairing a physician's ability to differentiate eye structures.

One such tool is a set of user-selectable "gamma curves." A gamma curve basically describes a display characteristic such as brightness as a function of echo signal intensity (the term brightness as used herein encompasses the location of a shade of grey on a grey scale). One such gamma curve in the Advent A/B™ System simply equates brightness with signal intensity in a linear fashion. The Advent A/B™ System also provides non-linear curves such as an "S Curve." The "S Curve" gamma curve has a relatively small slope at low and high signal intensities and has a relatively large slope at intermediate signal intensities. All the gamma curves are monotonic (i.e. the slope of each gamma curve is either always positive or always negative). Though the system contains color output ports, the image is monochromatic. The user can select a single color (e.g. white, sepia, etc.), which is displayed with varying degrees of brightness at different points in the image depending on the different echo signal intensities.

The known version of the Advent A/B™ System also provides a "gain knob" to help the user alter the image. By turning the knob, the user adjusts a constant or proportionality associated with any one of the gamma curves, so that the brightness that the gamma curve associates with every echo signal intensity is either increased or decreased.

The user selectable gamma curves and the gain knob allow the user to increase the visual contrast between different features of interest in the image and aid the user in the search for structure boundaries.

The Advent A/B™ System also supports "temporal averaging." Temporal averaging consists of storing ultrasound signal data for each image point over multiple scans and creating an image where each image point's shade of grey depends on the average value of the image point over the multiple scans.

An article by Gonzalo R. Diaz entitled "Ultrasound Color Imaging" suggests strategically adding color hues to ultrasound images that also include shades of grey. In particular, the article suggests that a user be allowed to substitute one or more color hues for one or more grey shades. The article states that the colored regions in the display provide good contrast against the remaining, predominately grey image. An accompanying color photograph entitled "Eye Ultrasound" includes various grey shades along with certain regions colored with various color hues. It appears that some closely similar hues were substituted for some closely similar grey shades. There does not appear to be a continuous gradation from the grey shades to the color hues; rather the image appears to abruptly juxtapose grey shades with color hues.

Certain corneal topography systems create color coded topographical maps that use different colors to show different amounts of deviation from an ideal surface. Doppler ultrasound imaging systems have used color to represent blood velocity. Certain magnetic resonance imaging (M.R.I.) systems and computer aided tomography (C.A.T.) scanners use multi-colored images to help physicians differentiate structures of interest.

SUMMARY OF THE INVENTION

It is an object of the invention to provide an improved apparatus and techniques for ophthalmic ultrasound imaging.

One aspect of the invention provides a system for producing visual representations of eye structures that includes an ultrasonic transducer, a processor, and a display device. The ultrasonic transducer transmits ultrasound signals into eye structures, receives ultrasound signals reflected by the eye structures, and sends electronic signals representative of the received ultrasound signals to the processor. The processor translates the electronic signals into image data representing a non-background portion of an image for display by the display device by correlating each value of a parameter of the electronic signals (e.g. each value of echo signal intensity) with one of a plurality of multichromatic color hues in accordance with a continuous gradation of the multichromatic color hues that forms the entirety of the non-background portion of the image.

The created image can convey a large amount of information because the human eye easily differentiates among a vast variety of color hues, and thus a physician can detect subtle changes in echo signal intensities in an image that is entirely formed from a continuous gradation of different color hues. The number of color hues in the continuous gradation is limited only by the hardware displaying the image. Further, a physician viewing an image colored in accordance with the continuous gradation of color hues can intuitively associate the "hotter" red color hues with greater echo intensities and the "cooler" blue color hues with lesser ones.

According to another aspect of the invention, the processor translates the electronic signals from the ultrasonic transducer into data representing an image for display on the display device by correlating different values of a parameter of the electronic signals, such as echo signal intensity, with different values of a display characteristic, such as brightness, in accordance with a gamma curve at least a portion of which is substantially continuous and non-monotonic.

Substantially continuous non-monotonic gamma curves have the advantage of creating high visual contrast between eye structures having small differences in echo signal intensity. These curves can also filter out background noise and unwanted detail from the image. These non-monotonic gamma curves can increase resolution, which is defined as the ability to identify structures in close proximity to each other. Described herein are several substantially continuous non-monotonic gamma curves tailored to aid physicians in viewing pathologies of different eye regions.

In another aspect of the invention, the processor translates the electronic signals from the ultrasonic transducer into data representing a multi-colored image for display on the display device by correlating different values of a first parameter of the electronic signals with different color hues and by correlating different values of a second parameter of the same electronic signals with different degrees of color hue brightness. For example, the color hue of an image point might represent the phase of the ultrasound signals while the point's brightness might indicate the echo signal intensity.

This aspect of the invention can aid physicians in determining eye structure boundaries. Color coding the phase information, for example, can inherently result in an image where the eye lens anterior surface would be outlined in red while the eye lens posterior surface would be outlined in green.

According to another aspect of the invention, the processor translates the electronic signals from the ultrasonic transducer into data representing an image for display on the display device, the translation including processing of phase information of the electronic signals.

As described above, images displaying phase information, represented by either an image point's color hue or an image point's brightness, potentially emphasize eye structure boundaries by displaying the anterior and posterior surfaces of the structure in different display characteristics. Further, processing of phase information can aid a physician in identifying where reverberation echoes have caused the image to indicate structures where none exist.

According to another aspect of the invention, the processor translates the electronic signals from the ultrasonic transducer into data representing an image for display on the display device by translating the electronic signals into the data representing the image, where the translation includes processing time persistence information of the electronic signals.

Display of time persistence information enables a physician to detect structures moving in the eye. This is particularly useful when searching for structures floating in the vitreous. For example, the color hue of a particular point on a displayed image might represent echo signal intensity and the brightness might represent the time persistence of the echo signal.

Numerous additional objects, advantages, and features of the invention will become apparent from the following detailed description in conjunction with the drawings and the claims.

DETAILED DESCRIPTION

Figure 1:
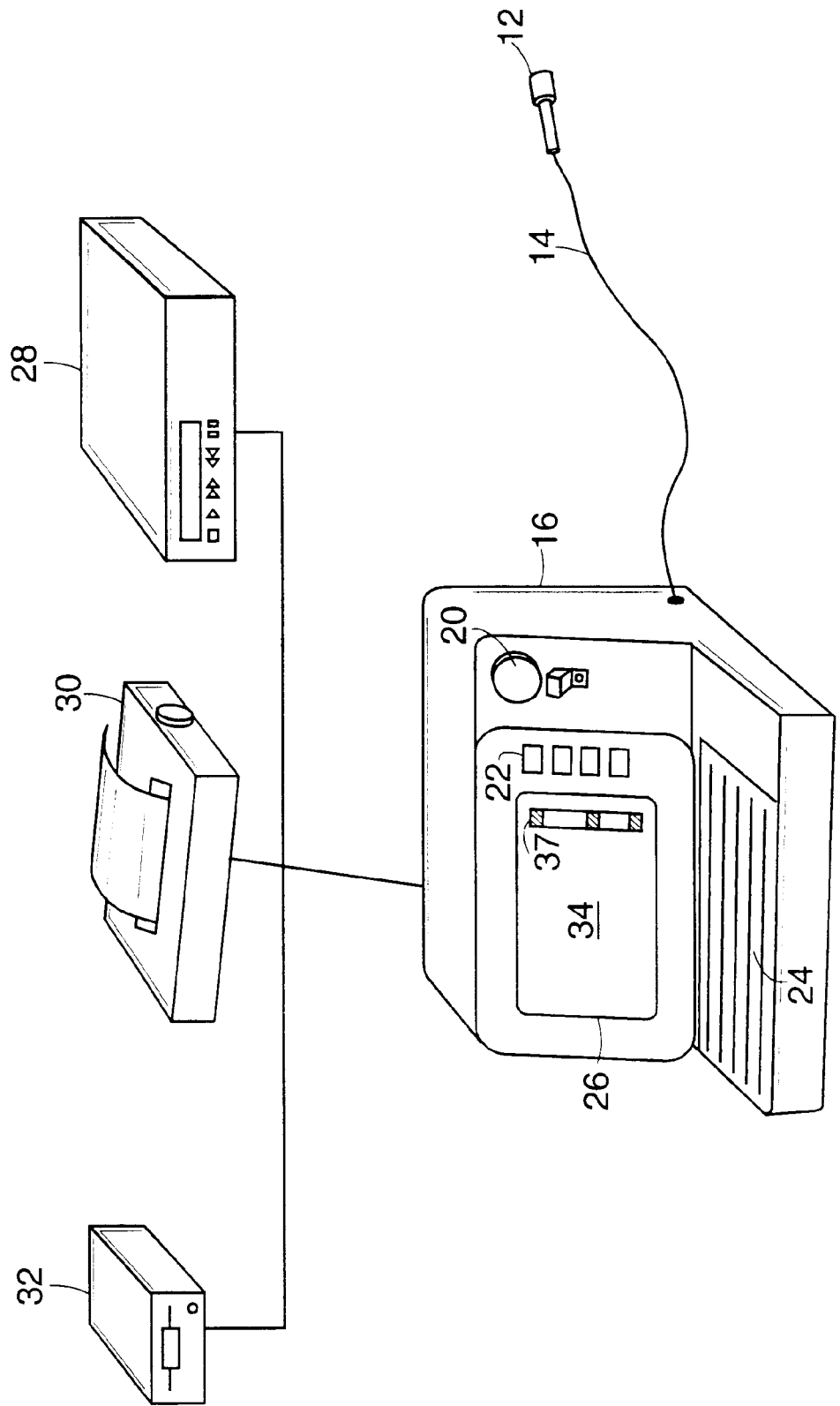
FIG. 1 is a drawing of an ultrasound imaging system in accordance with the invention.

With reference to FIG. 1, an ultrasonic imaging system according to the invention includes an ultrasonic transducer 12 and a processing terminal 16 that includes a central processor and a display device such as a monitor 26. In operation of the system, a physician places the ultrasonic transducer 12 near a patient's closed eye, and the ultrasonic transducer 12 emits ultrasound waves into the eye and receives echo signals from the emitted ultrasound waves. The echo signals indicate changes in impedance in eye structures at particular locations. Greater echo signal intensities indicate greater changes in impedance. The echo signals also contain phase information. An echo signal with a positive phase represents a change from low to high impedance. Conversely, an echo signal with a negative phase represents a change from high to low impedance. Ultrasound transducer 12 sends analog electronic signals representing the echo signals to a processing terminal 16 via an electrical cable 14.

Processing terminal 16 contains pre-processing circuitry, a central processor, memory, a gain knob 20, a keyboard 24, a set of function keys 22, and a display device 26. The analog electronic signals sent from the ultrasonic transducer via cable 14 enter the pre-processor circuitry which pre-processes the analog electronic signals and causes digitized signal information to be stored in memory. The physician controls the pre-processor circuitry via connected keyboard 24, function keys 22, and gain knob 20. For example, through the keyboard 24 or function keys 22, the physician can specify that the pre-processor circuitry should examine a particular frequency of the signals received from transducer 12, and can specify that the pre-processor circuitry should examine only those electronic signals received from the transducer 12 that are representative of a particular range of depth within the eye structure. The physician can also specify "time gain" controls, which amplify echo signals produced from structures deeper in the eye to compensate for attenuation by intervening structures. The physician can also boost or attenuate signal information by turning gain knob 20 right or left. The pre-processor circuitry converts the pre-processed analog signal to digitized electronic signal information to be stored in memory. In other embodiments, the functions described above could be performed by the central processor after signal digitization, instead of by the pre-processor circuitry.

The central processor translates the digitized electronic signal information in memory into data representing an image 34. The user can control the translation by selecting from a set of gamma curves, discussed in depth later, via keyboard 24 or function keys 22. The central processor causes the image to be displayed on monitor 26. Alternatively, the processor could send the image to a printer 30 or store the image electronically on a VCR 28 or a computer storage device such as a disk drive 32.

Monitor 26 displays the image 34 created by the central processor's translation of the electronic signals and also displays gamma curve bar 37. The image is a B-Scan (a two dimensional representation of structures in the patient's eye as shown). Optionally, an A-Vector (a simple one dimensional amplitude graph) may be superimposed over the B-Scan. Gamma curve bar 37 graphically indicates how a user-selected gamma curve translates different values of a parameter of the electronic signal, such as different values of echo signal intensity into different values of a display characteristic such as color hue or monochromatic brightness.

The physician can zoom in and magnify an image section by issuing commands to the central processor via keyboard 24 or function keys 22. For example, a physician measuring retinal thickness may zoom in on a portion of a retina for closer examination. The physician can pan around the remaining image after zooming in or alternately have the central processor calculate the distance between two image points. The system also provides a "quad mode" that displays up to four images simultaneously for instant comparative analysis of sequential scans. Additionally, the system provides a "window mode" that displays split-screen images, thereby providing a view of the full eye and surrounding tissue as well as a magnified view of a user-defined window area.

Figure 2:
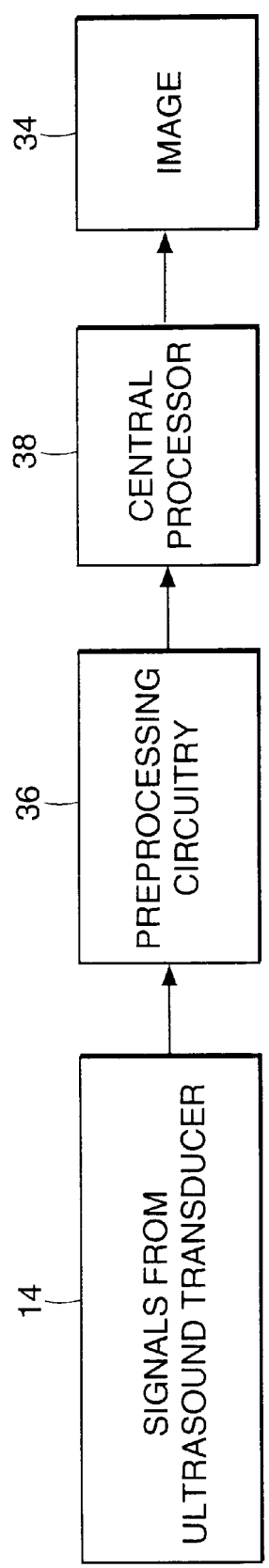
FIG. 2 is a flowchart illustrating how the ultrasound imaging system transforms ultrasound signals into an image.

With reference to FIG. 2, which provides an overview of how the system processes the ultrasound echo signals it receives, analog electronic signals from the ultrasonic transducer 14 enter the pre-processor circuitry 36, which performs user-specified functions on the analog electronic signal such as time gain control and signal boosting or attenuating as controlled by gain knob 20. Pre-processor circuitry 36 sends digitized data representing the electronic signal to central processor 38. The central processor then translates the data into image data for display on the monitor 34 using the user-selected gamma curve.

Figure 3:
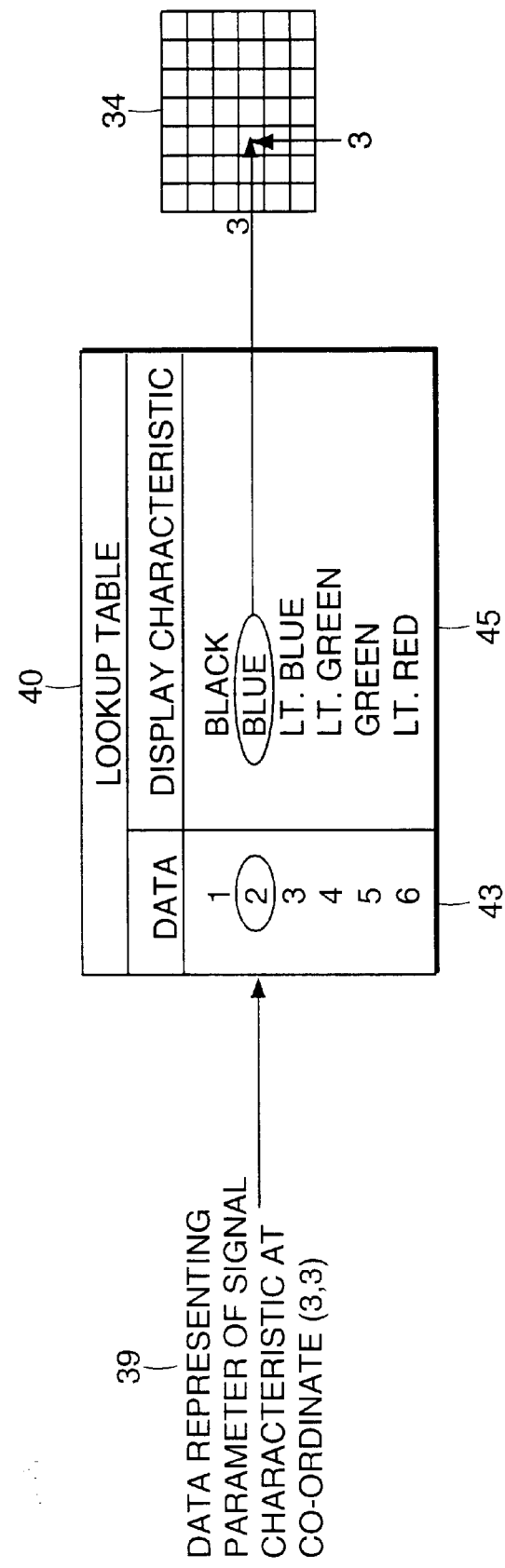
FIG. 3 is a flowchart illustrating how the ultrasound imaging system translates ultrasound signals into color hues using a lookup table.

With reference to FIG. 3, which provides an overview of how the central processor uses a gamma curve lookup table for color display, the central processor receives data 39 representing a signal characteristic such as echo signal intensity at a particular co-ordinate and searches a lookup table 40 for a corresponding display characteristic value. Lookup table 40 can be illustrated as shown in FIG. 3 as including columns for the data values 43 and display characteristics 45. When the central processor finds a row of the lookup table 40 corresponding to data received by the processor, the central processor retrieves a corresponding display characteristic value (in this case color hue) and causes the particular coordinate of image 34 to have the display characteristic specified by the lookup table 40.

Figure 4:
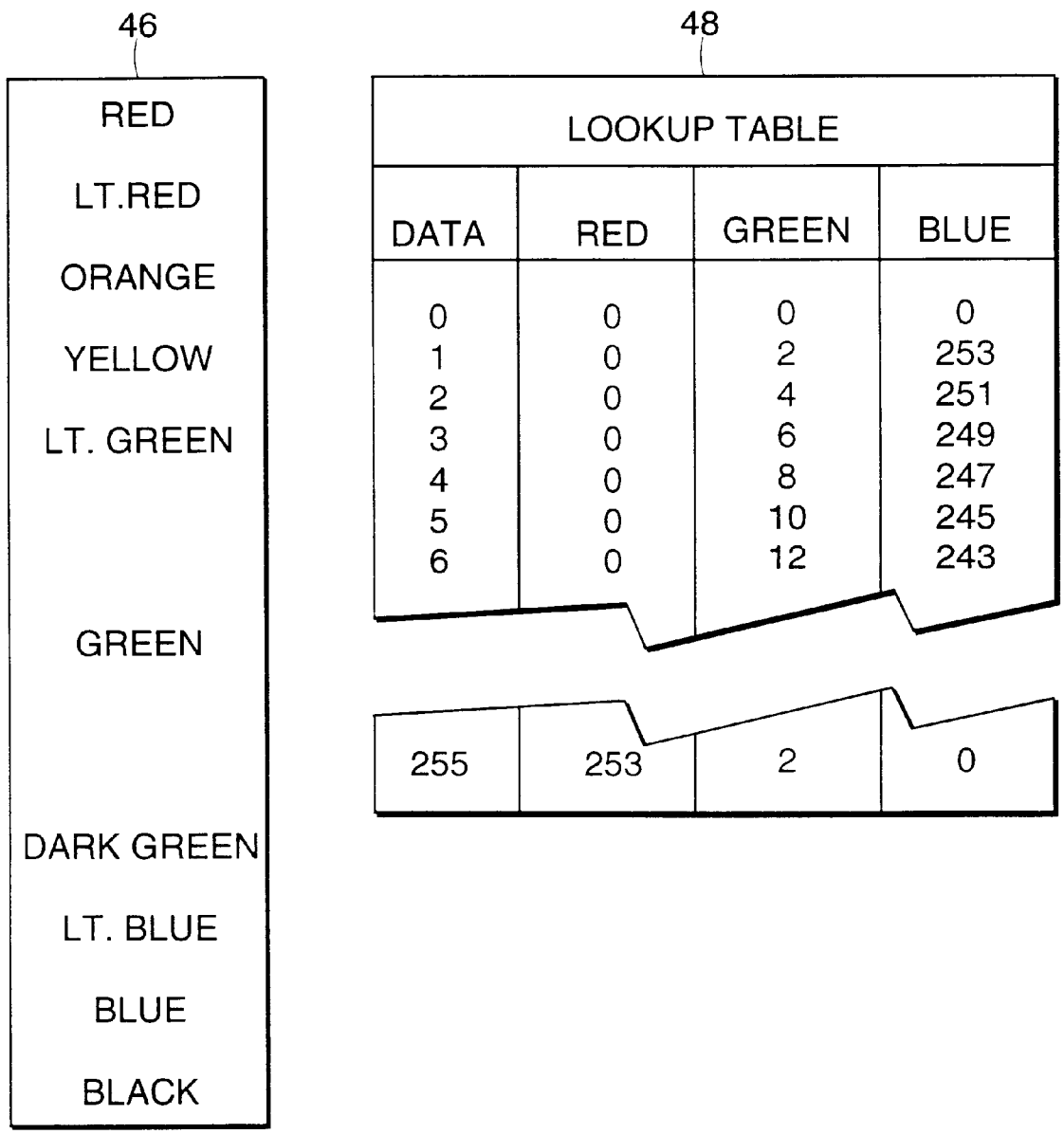
FIG. 4 is a lookup table and gamma curve bar of a multi-color gamma curve with a continuous gradation of color hues.

With reference to FIG. 4, the processing terminal stores the color gamma curve lookup table 48, which is used for producing images that are displayed in accordance with its associated gamma bar 46 which is displayed on the monitor. Gamma bar 46 gradually changes color hues from black to red. As in color weather maps, this gamma bar displays stronger echo signal intensities in "hotter" colors such as red and displays weaker echo signal intensities in "cooler" colors such as blue. The intuitiveness of this color scheme quickly allows a physician to understand the meaning of the different color hues.

The ultrasound transducer may have a dynamic range of about 100 dB, which means that the strongest possible echo signal is about 100,000 times the weakest possible echo signal. Thus, if the weakest signal is thought of as an increment of one, there are a total of about 100,000 different increments of possible echo signal intensities. The use of a continuous gradation of color hues makes it possible for the physician to readily discern amongst a large number of these possible echo signal intensities, because the human eye has a strong ability to distinguish color hues from one another. For example, one embodiment of the processor includes an 8-bit converter that enables display of 256 different color hues, and another embodiment includes a 12-bit processor that enables display of 4096 different color hues. Because the gradation of color hues is continuous over the entire range of possible echo signal intensities, the image provides to the physician a vast amount of information pertaining to the entire range of echo signal intensities.

Figure 5:
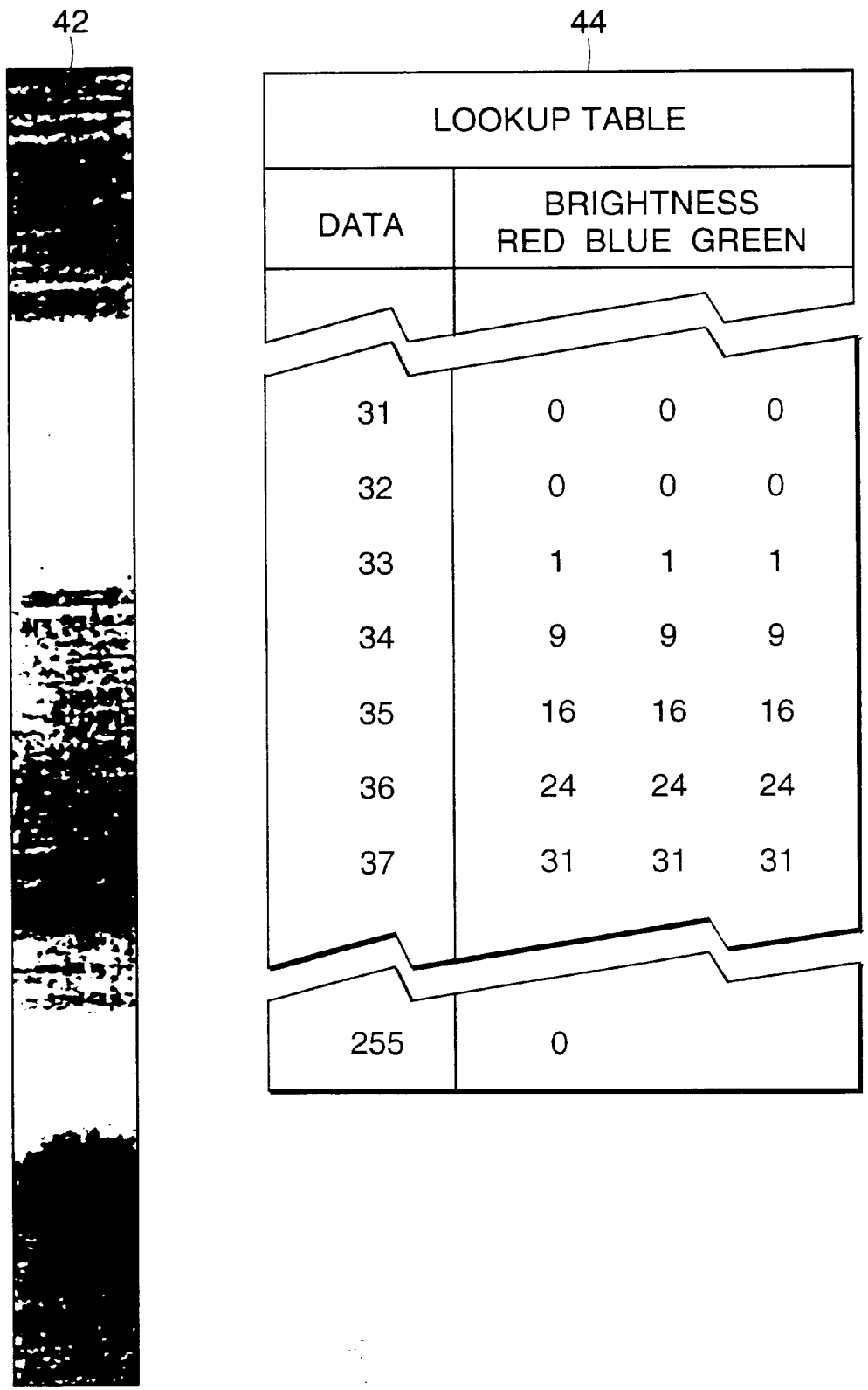
FIG. 5 is a lookup table and gamma curve bar of a gamma curve at least a portion of which is substantially continuous and non-monotonic.

With reference to FIG. 5, the processing terminal also stores a gamma curve lookup table 44 that contains data for producing images that are displayed in accordance with gamma bar 42. The particular gamma bar 42 illustrated in FIG. 5 is non-monotonic; that is, instead of continually increasing or decreasing in brightness, the curve contains multiple regions of high brightness that gradually fade into intervening dimmer regions. The bar also contains completely black regions. Information that falls in the black regions is filtered out, thereby allowing the physician to suppress display of uninteresting structures that interfere with the display of interesting structures. Additionally, the alternating brighter and dimmer regions provide high visual contrast between structures with otherwise close echo signal intensity values. The processing terminal stores several non-monotonic gamma curve lookup tables tailored for examining particular regions of the eye, including an "Anterior" gamma curve, a "Vitreous/Retina" gamma curve, and a "Retina/Orbit" gamma curve. The Anterior gamma curve causes the profiles of the cornea, iris, and ciliary body to be crisply outlined, thereby creating an image that delineates the anterior chamber angle of the eye. This is of utmost importance to the glaucoma specialist and cataract surgeon wishing to visualize a cataract or the placement of a lens implant. The Vitreous/Retina gamma curve causes visualization of structures floating within the vitreous to be enhanced. Thus, blood, vitreous condensate, foreign objects, and inflammatory response cells trapped in the vitreous can be seen in exaggerated relief. The Retina/Orbit gamma curve causes the appearance of the retina, choroid, sclera, and orbital fat to be emphasized. This gamma curve allows a physician to look deep into the retina where exaggerated tissue differentiation is particularly useful in making retina measurements. In another embodiment, the physician can define the physician's own gamma curve through a user-interface that allows the physician to specify where color hues or shades of grey appear in a gamma bar.

Ultrasound images can contain indications of background noise detected by the ultrasound transducer. The physician can eliminate some background noise through use of a "reject" function key (one of the function keys 22 shown in FIG. 1). A physician can elect to have the central processor modify any gamma curve such that small echo signal intensities translate to a uniform background display characteristic. By default, the background display characteristic is black.

Figure 6:
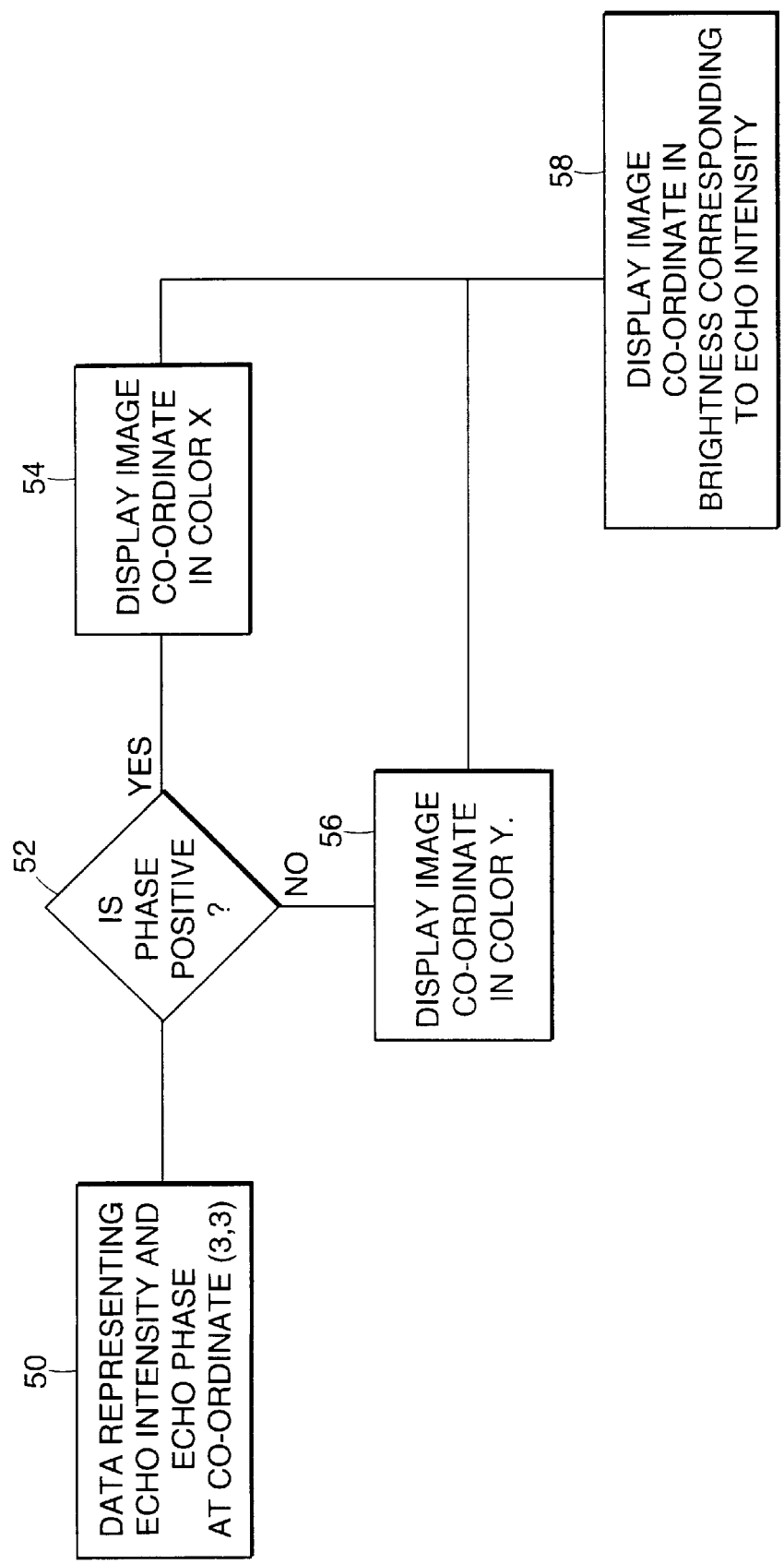
FIG. 6 is a flowchart illustrating how the ultrasound imaging system creates an image that represents phase data with color hues and echo signal intensity with brightness.

With reference to FIG. 6, which provides an overview of how the central processor constructs an image with phase information represented by color hues and echo signal intensity represented by brightness, data 50 representing echo signal intensity and phase at a particular co-ordinate is examined to check the sign of the phase 52. Positive phases, indicating a rise in impedance, are displayed in one color hue 54, for example, red, while negative phases, indicating a drop in impedance, are displayed in another 56, for example, green. The central processor causes brightness of the hue to correspond to the echo signal intensity 58. Brightening of color hues is accomplished by increasing each red, green, and blue component of the image point while keeping their ratio constant.

A physician can use color coded phase information to create an image in which an eye structure, such as an eye lens, would have its anterior surface appear in red while its posterior surface appears in green. Thus, the physician has valuable information indicating the presence of the structure boundaries. Other embodiments can use more than two color hues to represent the phase information.

Figure 7:
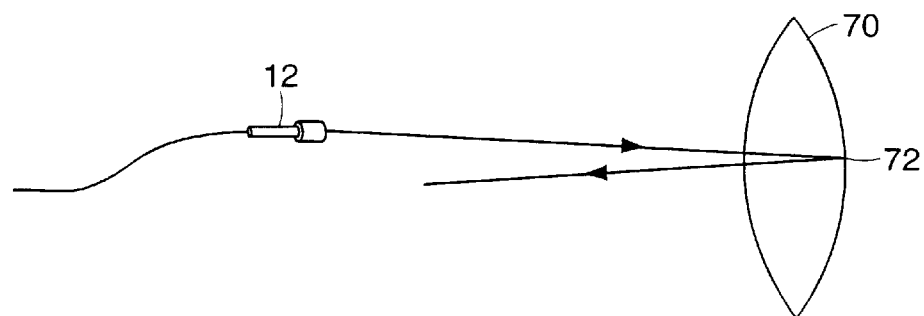
FIG. 7 is a drawing illustrating how an ultrasound signal travels from the ultrasonic transducer, to an eye structure, and back to the ultrasonic transducer.

With reference to FIG. 7, which illustrates the path of a possible ultrasound signal, the ultrasound transducer 12 sends an ultrasound signal into the eye to a lens posterior surface 72, which reflects the ultrasound signal back to the ultrasonic transducer due to the change in impedance from the interior of the lens 70 and the vitreous fluid behind the lens.

Figure 8:
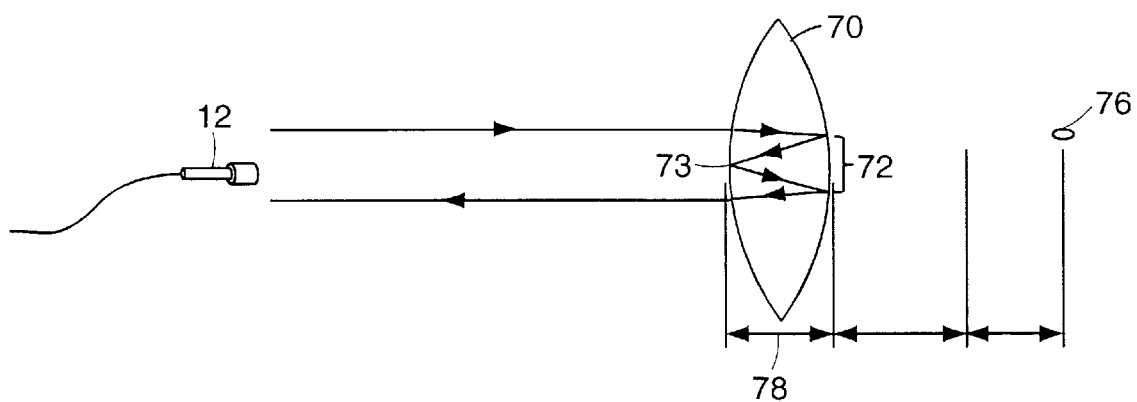
FIG. 8 is a drawing illustrating how a reverberation signal travels from the ultrasonic transducer, bounces back and forth between eye structures, and returns to the ultrasonic transducer.

With reference to FIG. 8, which illustrates the path of a reverberation echo signal, the ultrasound transducer 12 sends an ultrasound signal into the eye to the lens posterior surface 72, which reflects the ultrasound signal back toward the ultrasound transducer 12, but before reaching the ultrasound transducer 12, as in FIG. 7, the ultrasound signal is reflected back by the lens anterior surface 73. The ultrasound signal is again reflected by the lens posterior surface 72 and finally reaches the ultrasonic transducer 12. The ultrasound signal in FIG. 8 took much longer to reach the ultrasound transducer 12 than the ultrasound signal in FIG. 7 even though both were reflected by the same lens posterior surface 72. Ultrasound technology uses travel time as an indication of how far away a change in impedance occurred; hence, the central processor creates image data that indicates the presence of a non-existent structure 76. By color coding (or "brightness" coding) phase information, the resulting image can aid a physician in distinguishing real structures from phantom ones. For example, the image may outline the anterior surface of a lens in green. A physician can determine that similarly shaped green outlines behind the lens were produced by reverberation echo signals instead of real ones.

Figure 9:
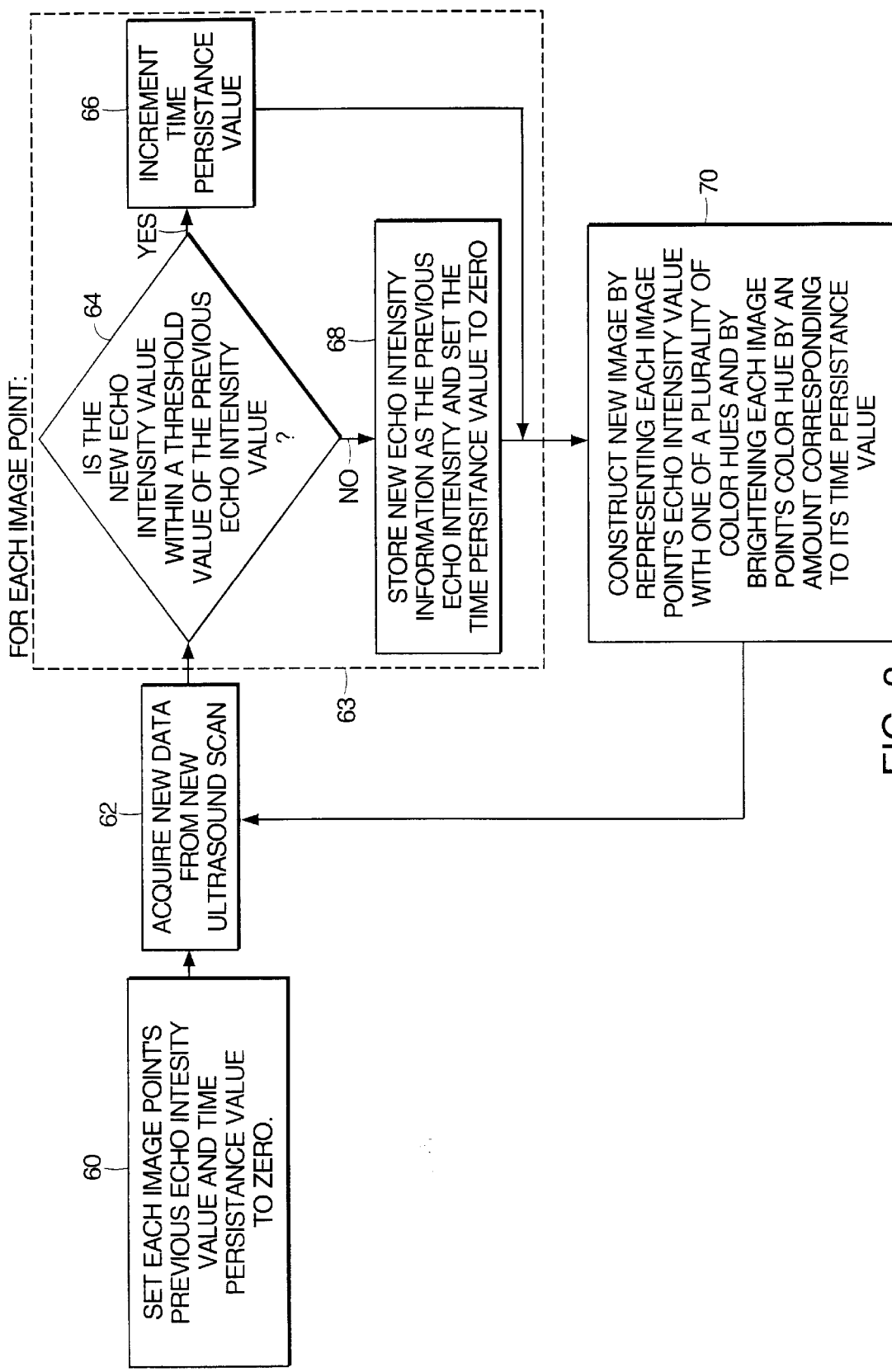
FIG. 9 is a flowchart illustrating how the ultrasound imaging system creates an image that represents echo signal intensity with color hues and time persistence with color hue brightness.
Figure 10:
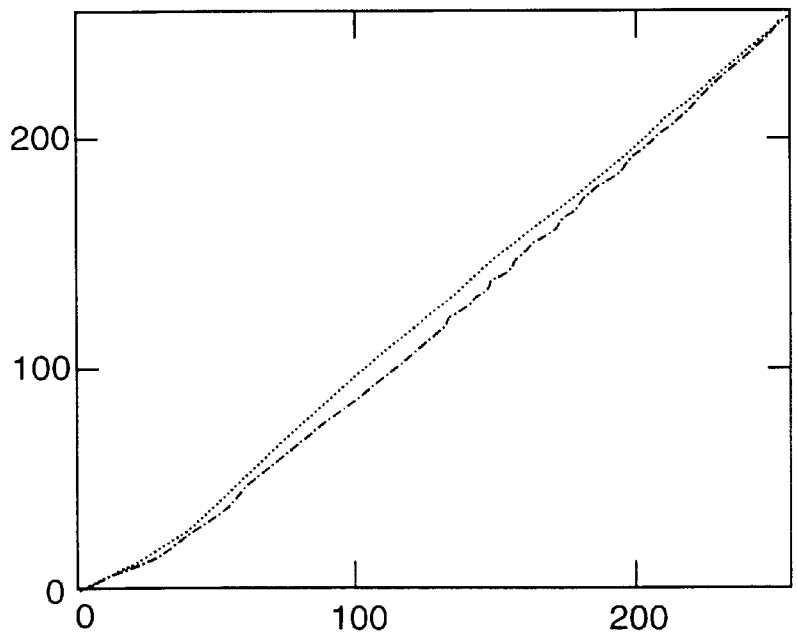
FIG. 10 is a graph of a linear gamma curve.
Figure 11:
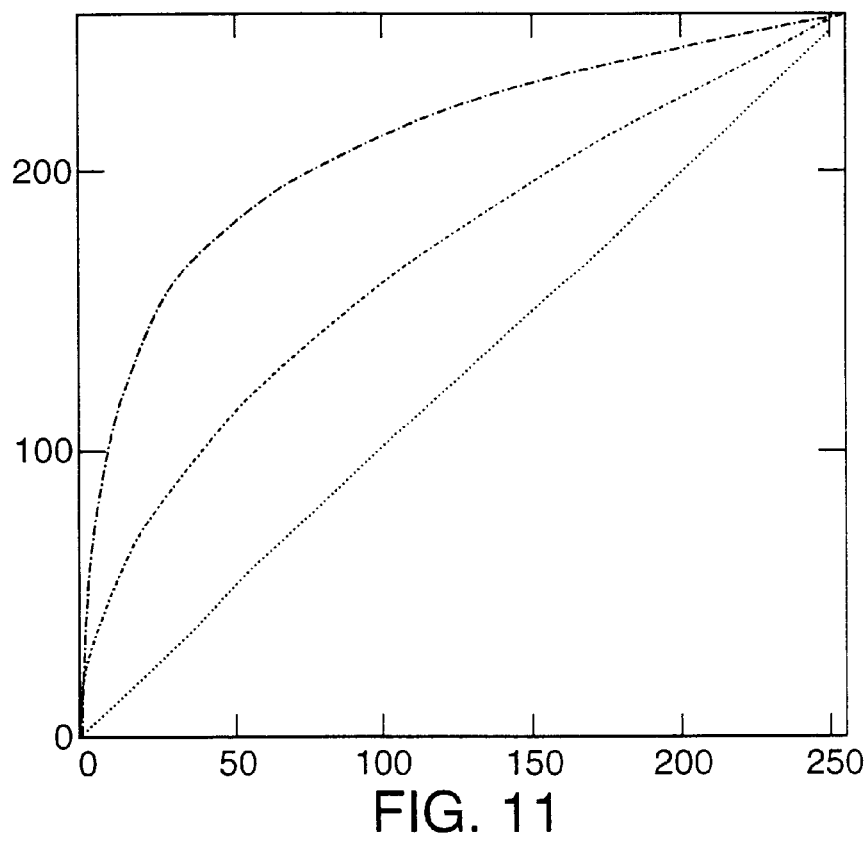
FIG. 11 is a graph of a logarithmic gamma curve.
Figure 12:
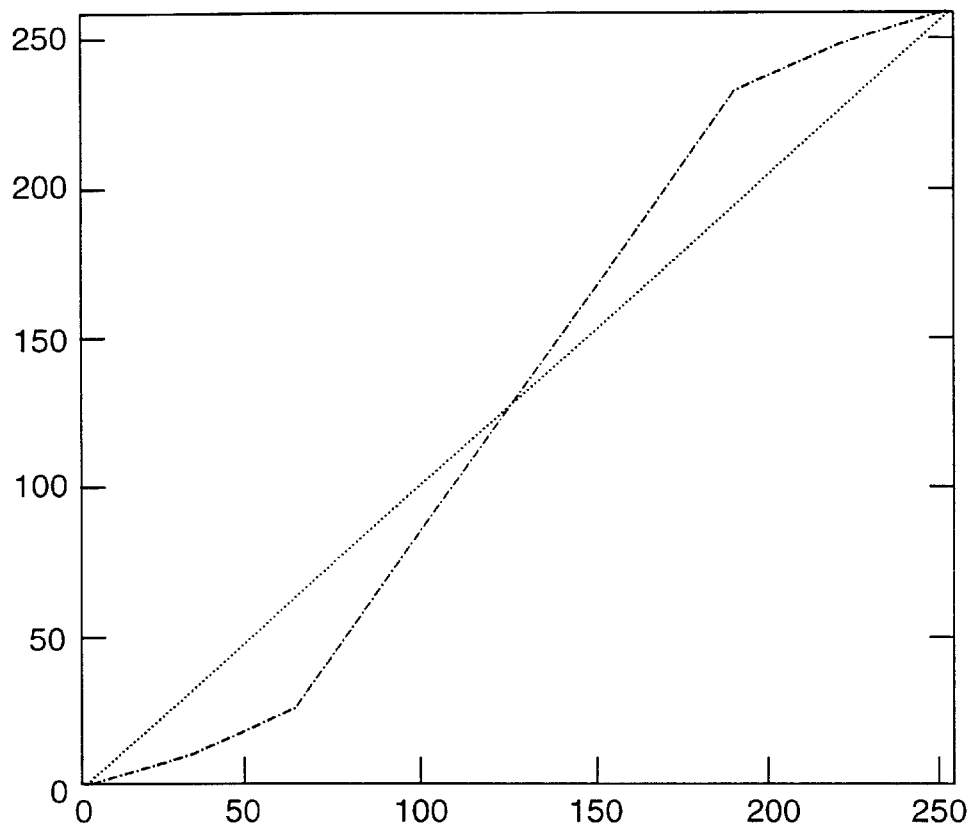
FIG. 12 is a graph of a "S-Curve" gamma curve.
Figure 13:
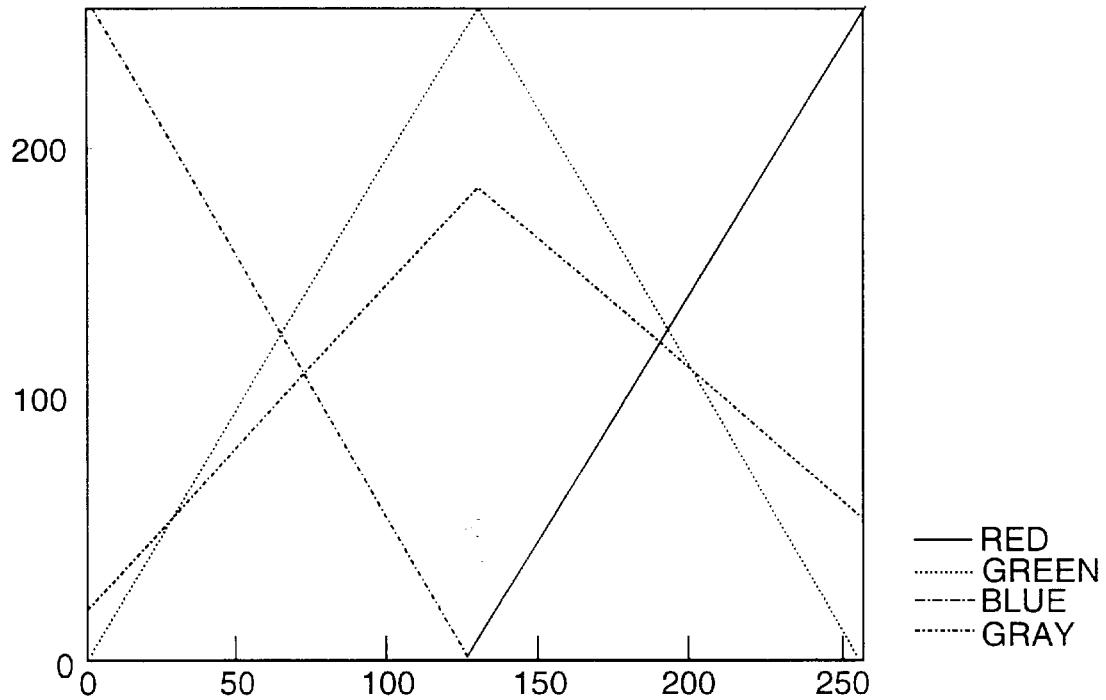
FIG. 13 is a graph of a multi-color gamma curve.
Figure 14:
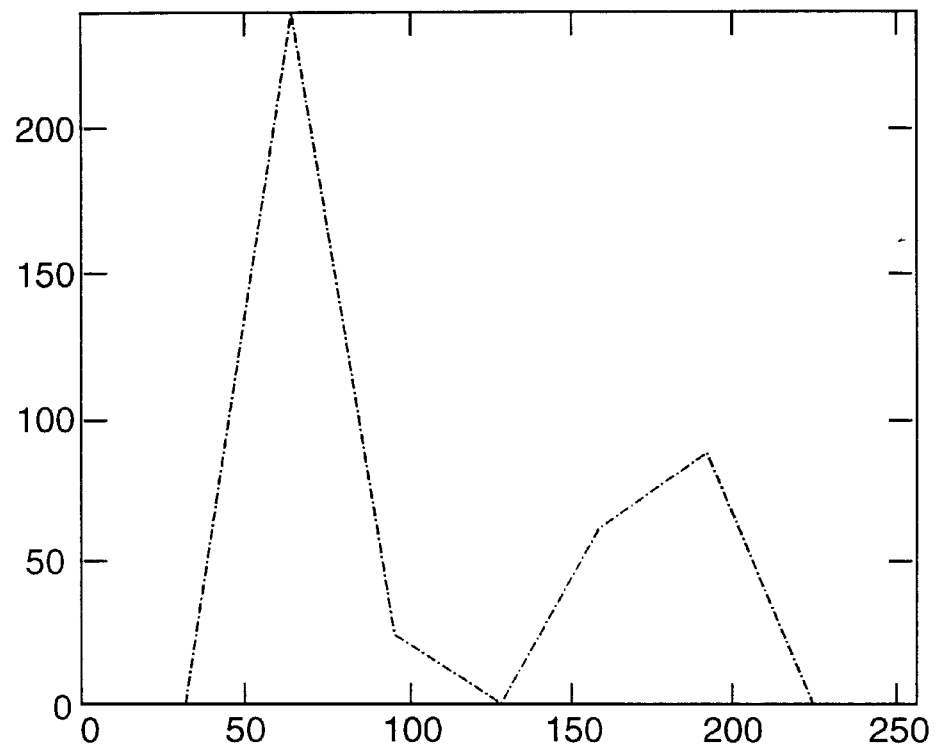
FIG. 14 is a graph of a gamma curve tailored to highlight anterior segment pathology (the "Anterior" gamma curve).
Figure 15:
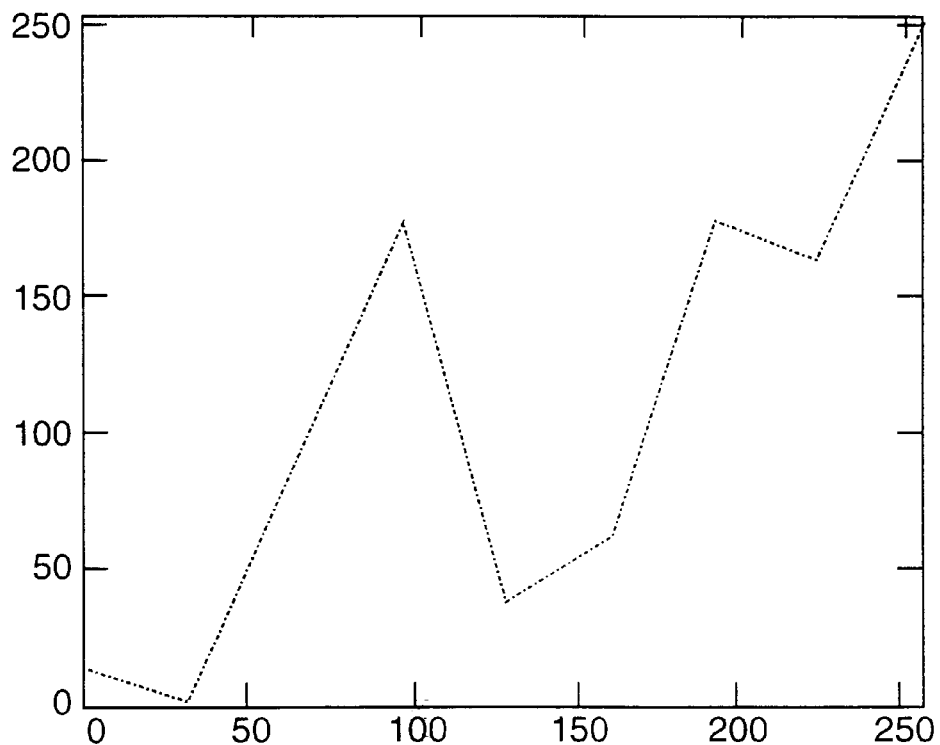
FIG. 15 is a graph of the gamma curve tailored to highlight vitreous or retinal segment pathology (the "Vitreous/Retina" gamma curve).
Figure 16:
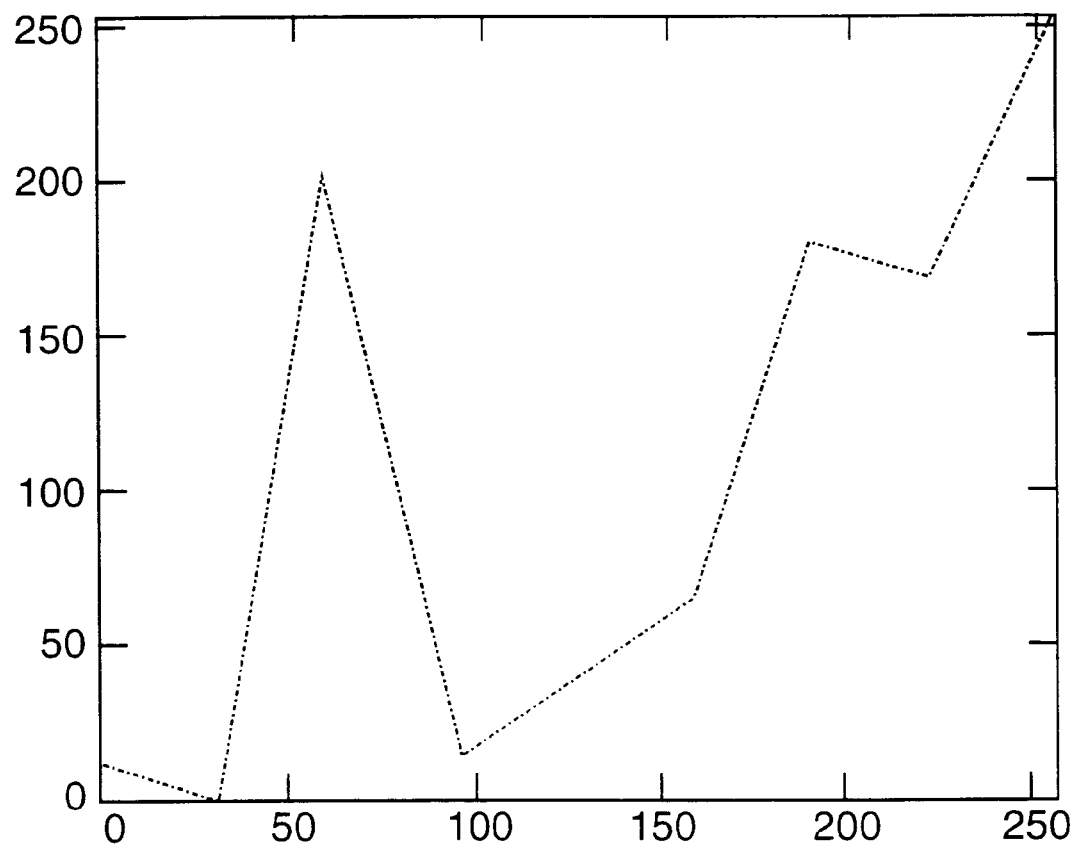
FIG. 16 is a graph of the gamma curve tailored to highlight retinal or orbital segment pathology (the "Retina/Orbit" gamma curve).
Figure 17:
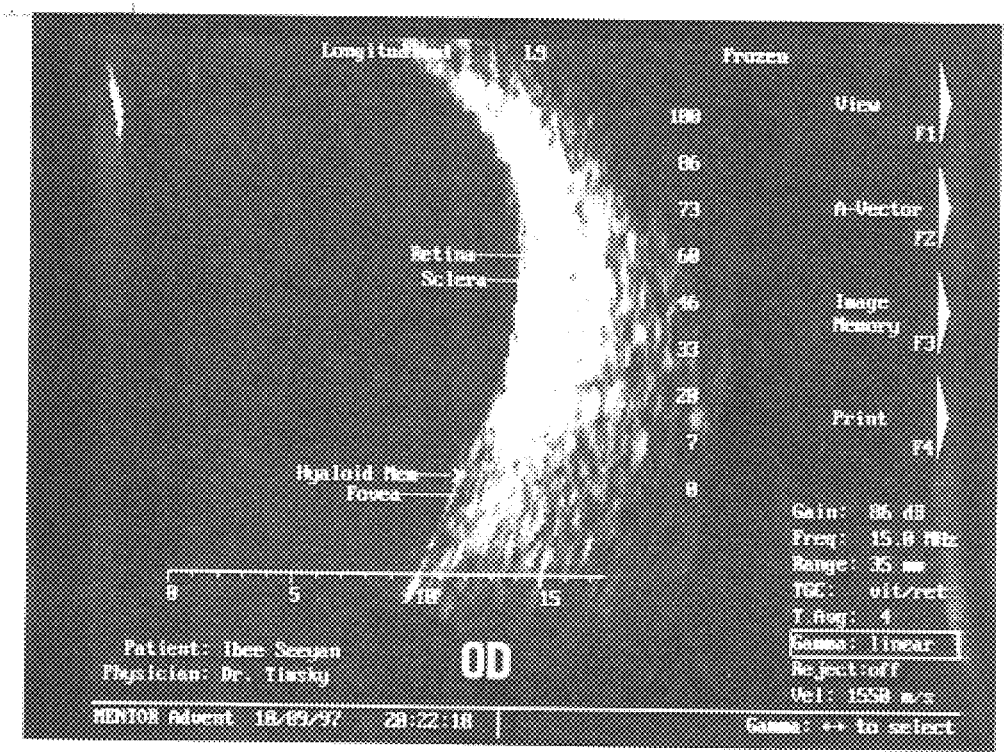
FIG. 17 is a photograph of a retina, sclera, and orbital fat created by selecting the linear gamma curve.
Figure 19:
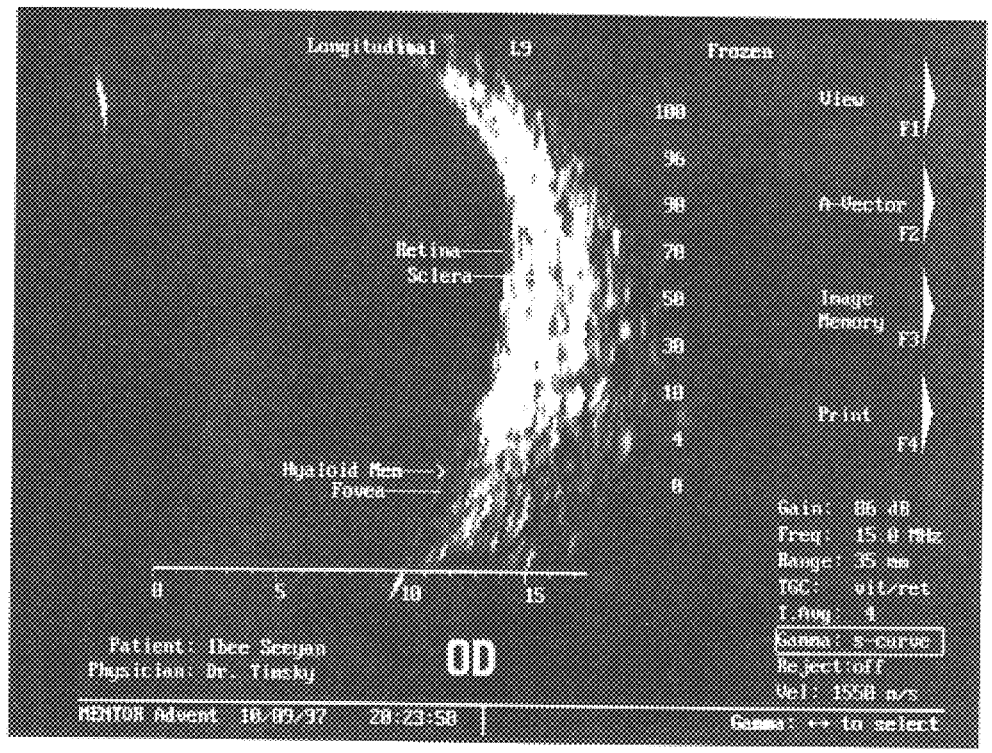
FIG. 19 is a photograph of the same retina, sclera, and orbital fat created by selecting the "S Curve" gamma curve.
Figure 18:
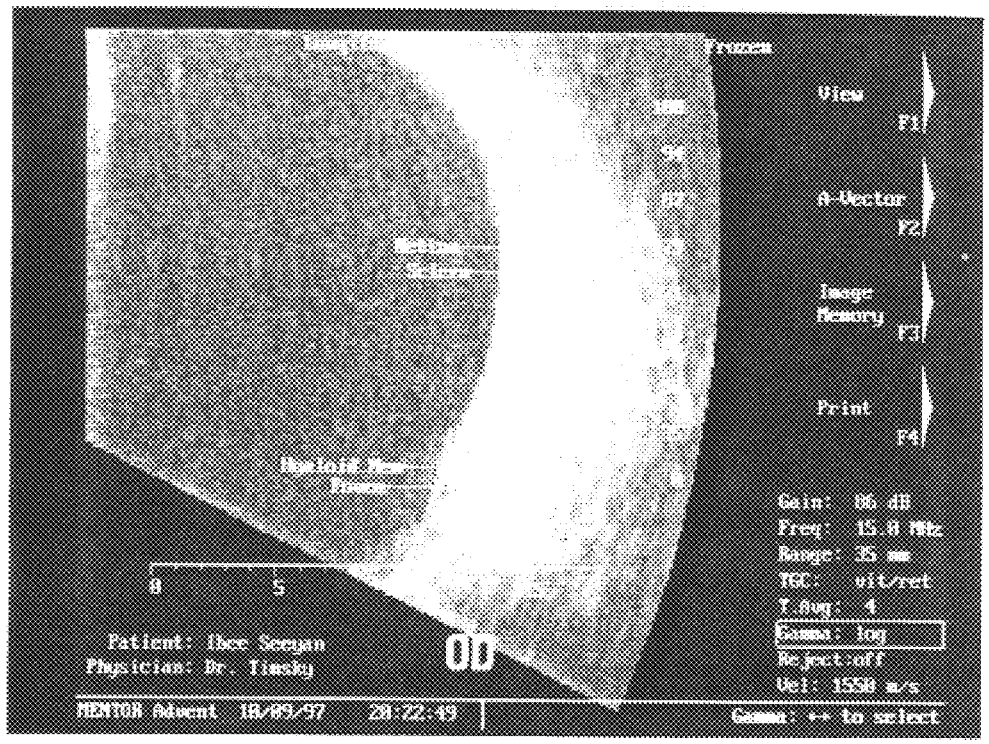
FIG. 18 is a photograph of the same retina, sclera, and orbital fat created by selecting the logarithmic gamma curve.
Figure 20:
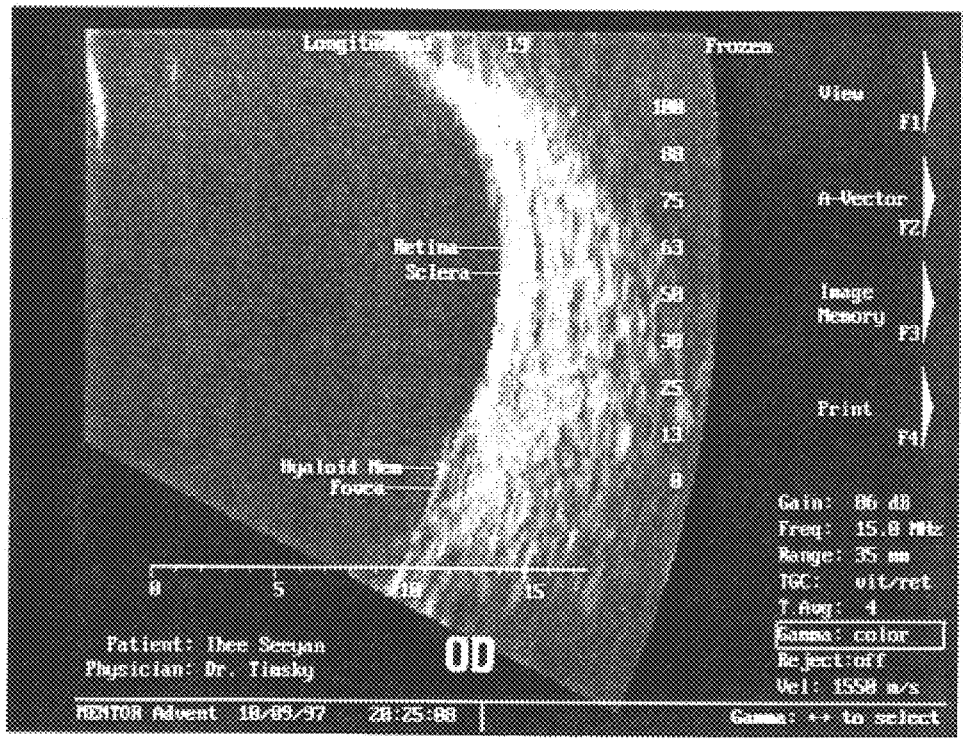
FIG. 20 is a black and white photograph of the same retina, sclera, and orbital fat created by selecting the multi-color gamma curve.
Figure 21:
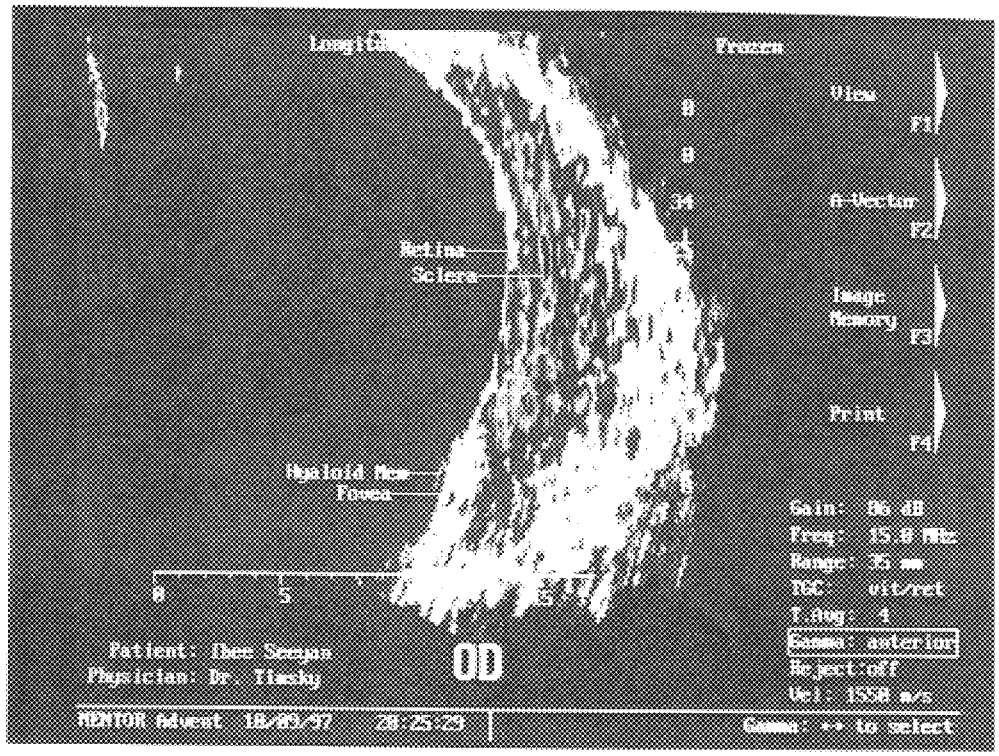
FIG. 21 is a photograph of the same retina, sclera, and orbital fat created by selecting the "Anterior" gamma curve.
Figure 23:
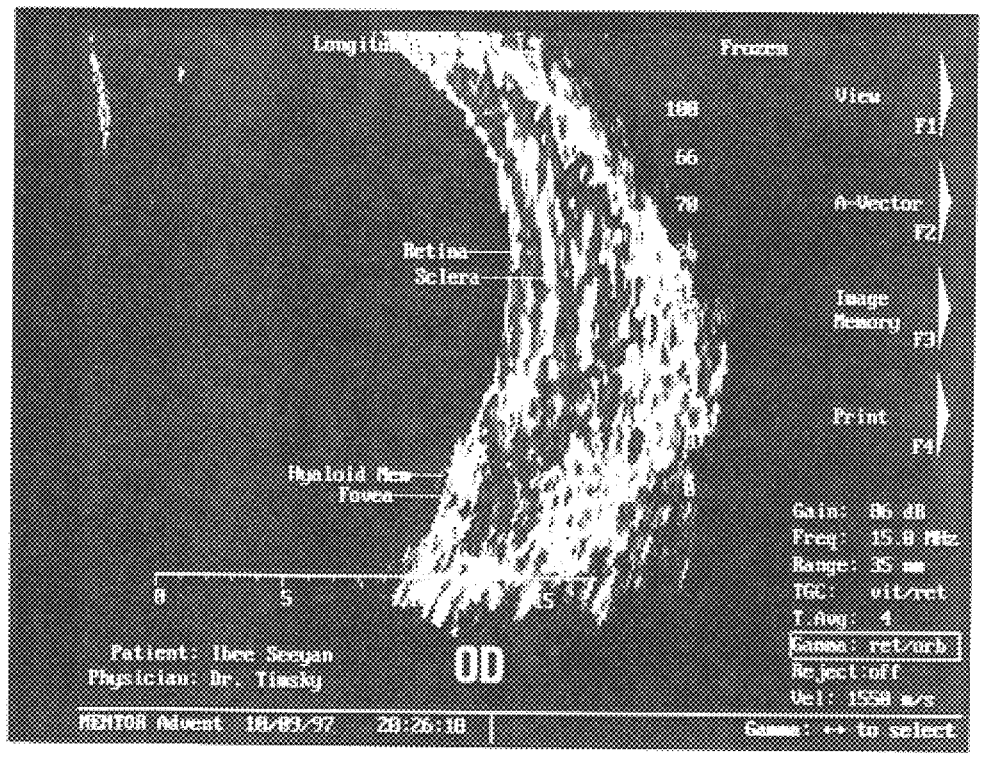
FIG. 23 is a photograph of the same retina, sclera, and orbital fat created by selecting the "Retina/Orbit" gamma curve.
Figure 22:
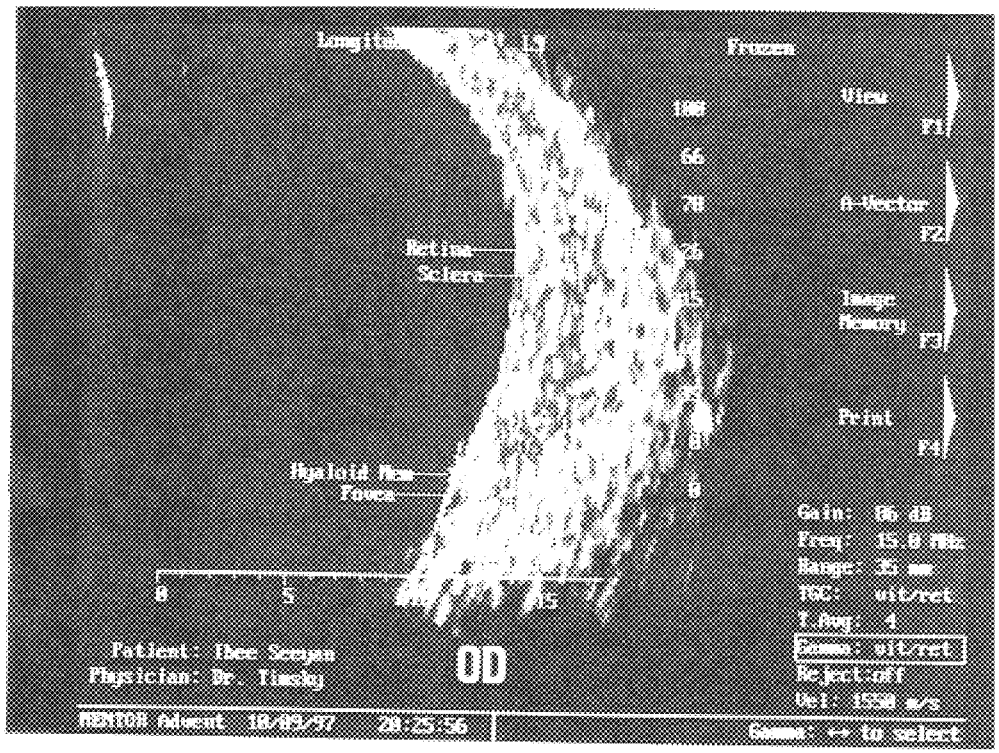
FIG. 22 is a photograph of the same retina, sclera, and orbital fat created by selecting the "Vitreous/Retina" gamma curve.
Figure 24:
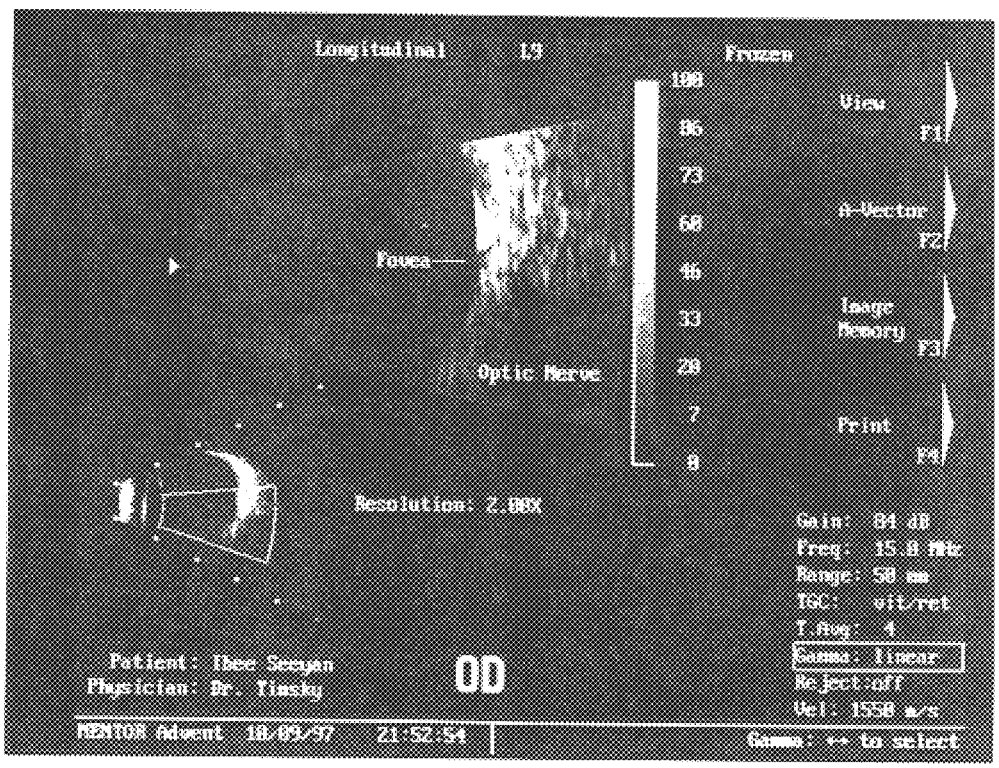
FIG. 24 is a window mode photograph of a fovea created by selecting the linear gamma curve.
Figure 25:
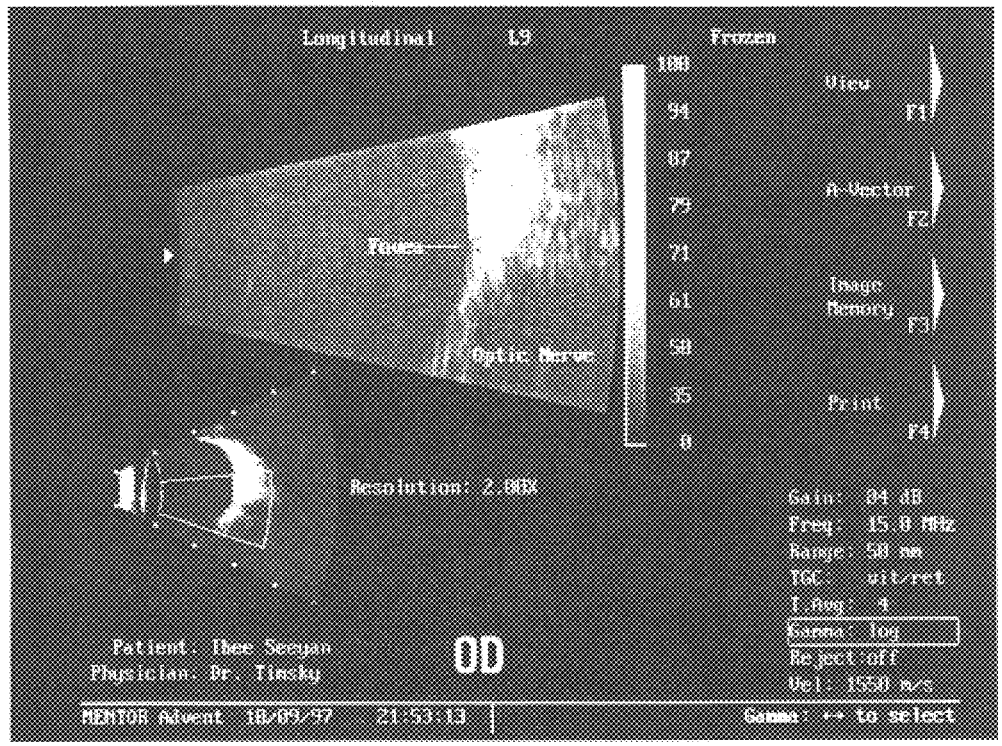
FIG. 25 is a window mode photograph of the same fovea created by selecting the logarithmic gamma curve.
Figure 27:
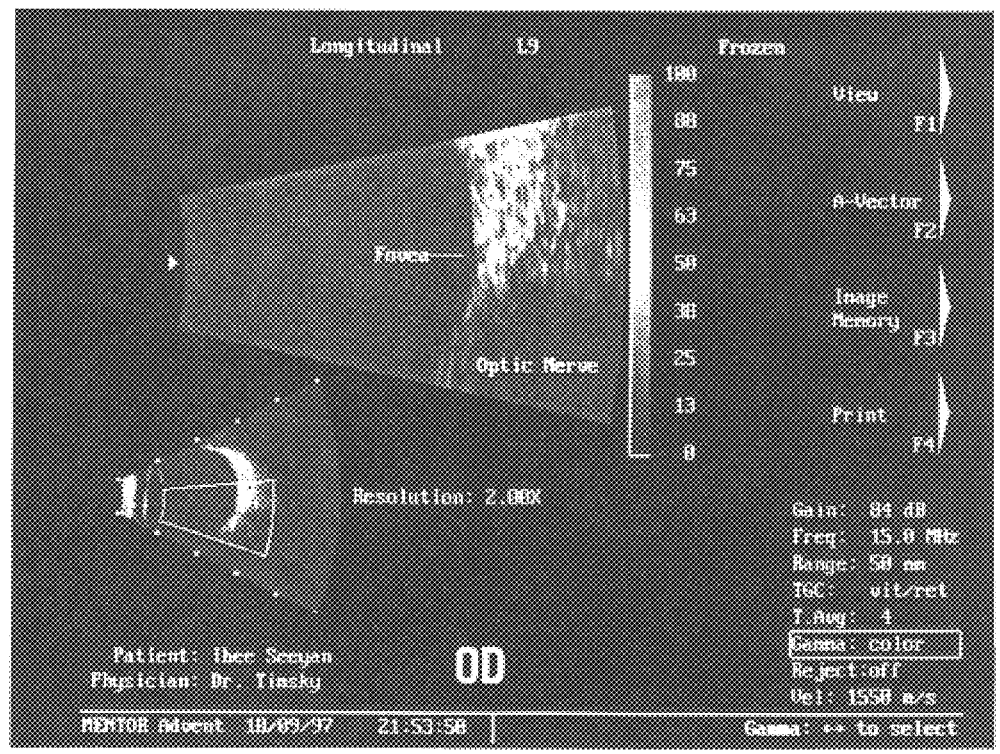
FIG. 27 is a black and white window mode photograph of the same fovea created by selecting the multi-color gamma curve.
Figure 26:
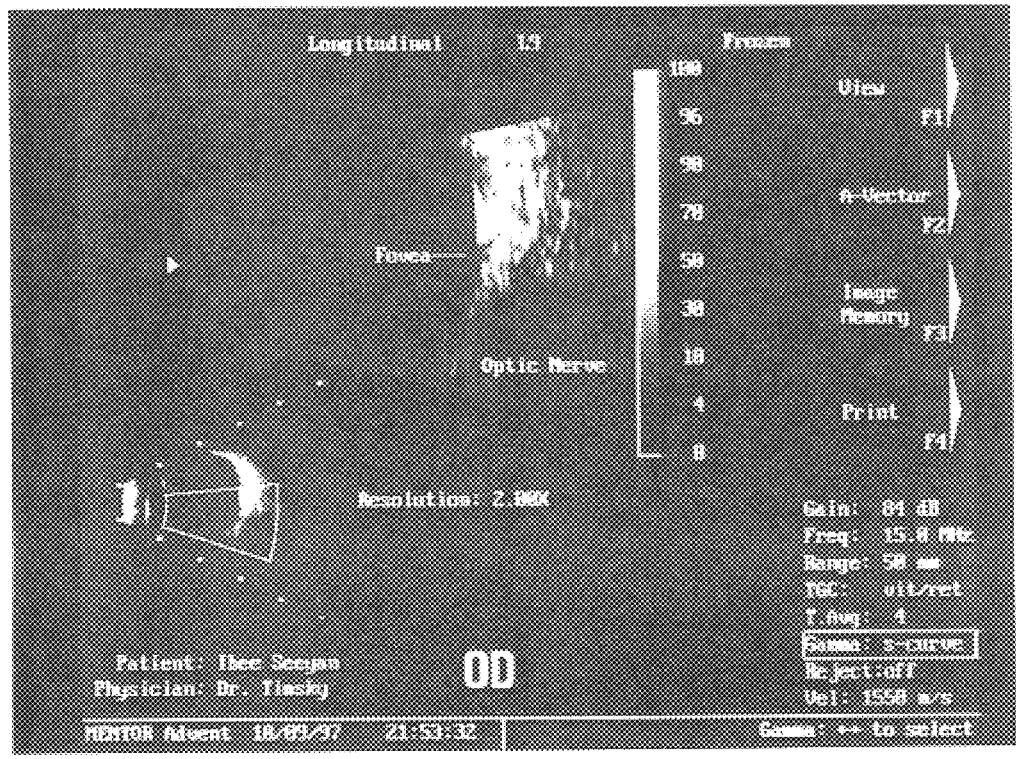
FIG. 26 is a window mode photograph of the same fovea created by selecting the "S-Curve" gamma curve.
Figure 28:
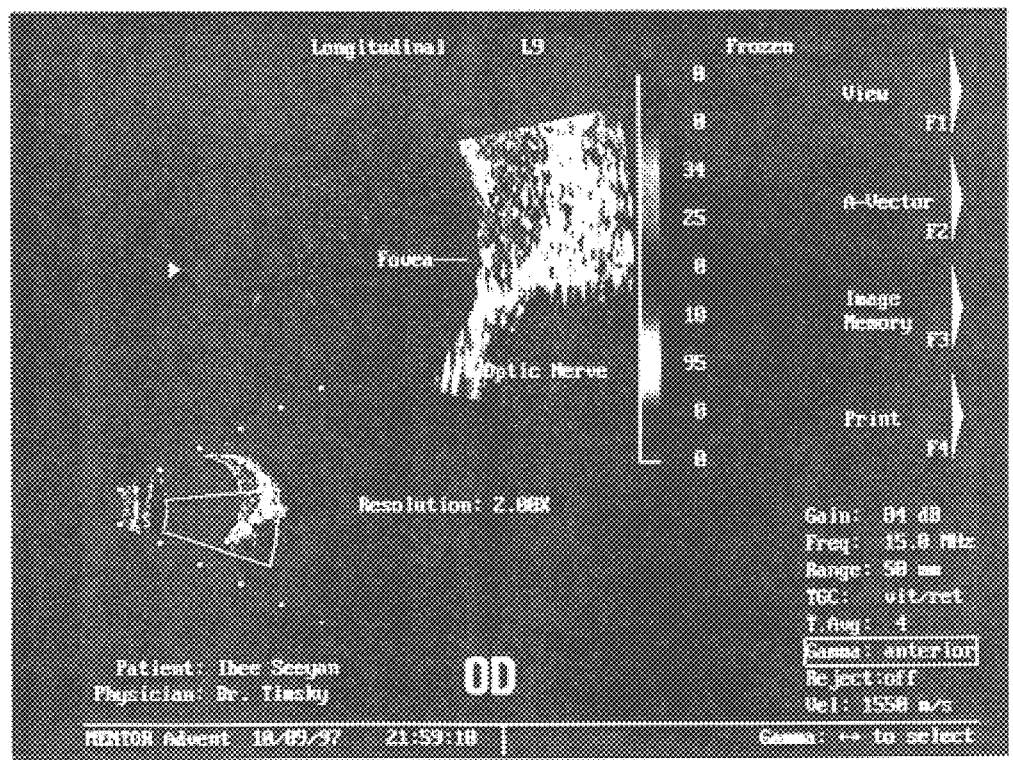
FIG. 28 is a window mode photograph of the same fovea created by selecting the "Anterior" gamma curve.
Figure 29:
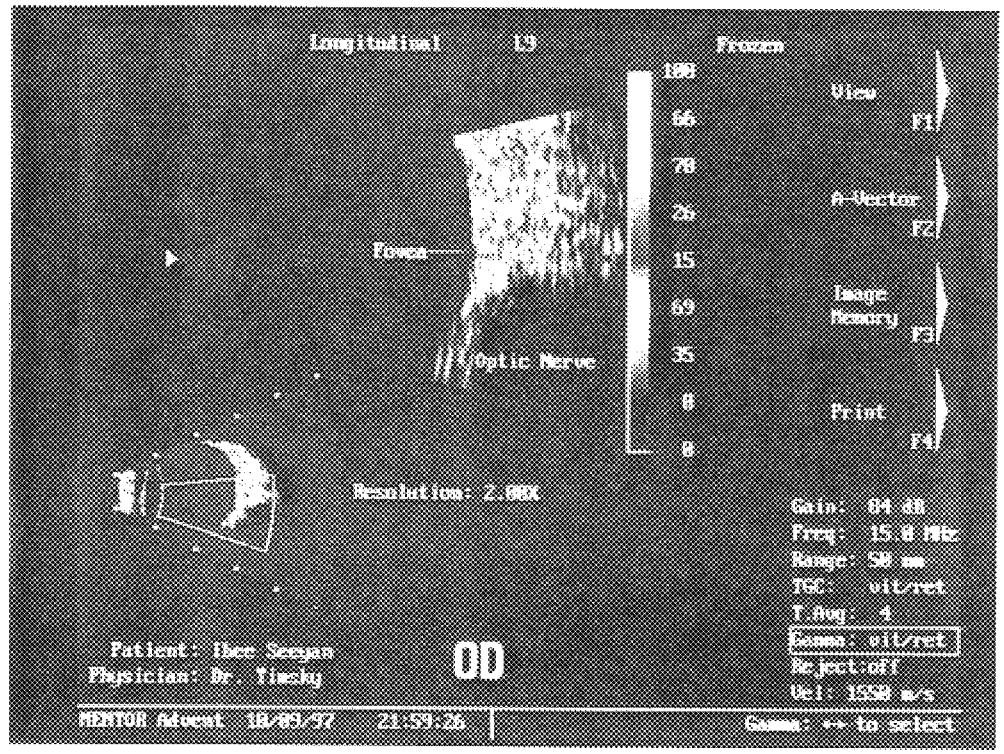
FIG. 29 is a window mode photograph of the same fovea created by selecting the "Vitreous/Retina" gamma curve.
Figure 31:
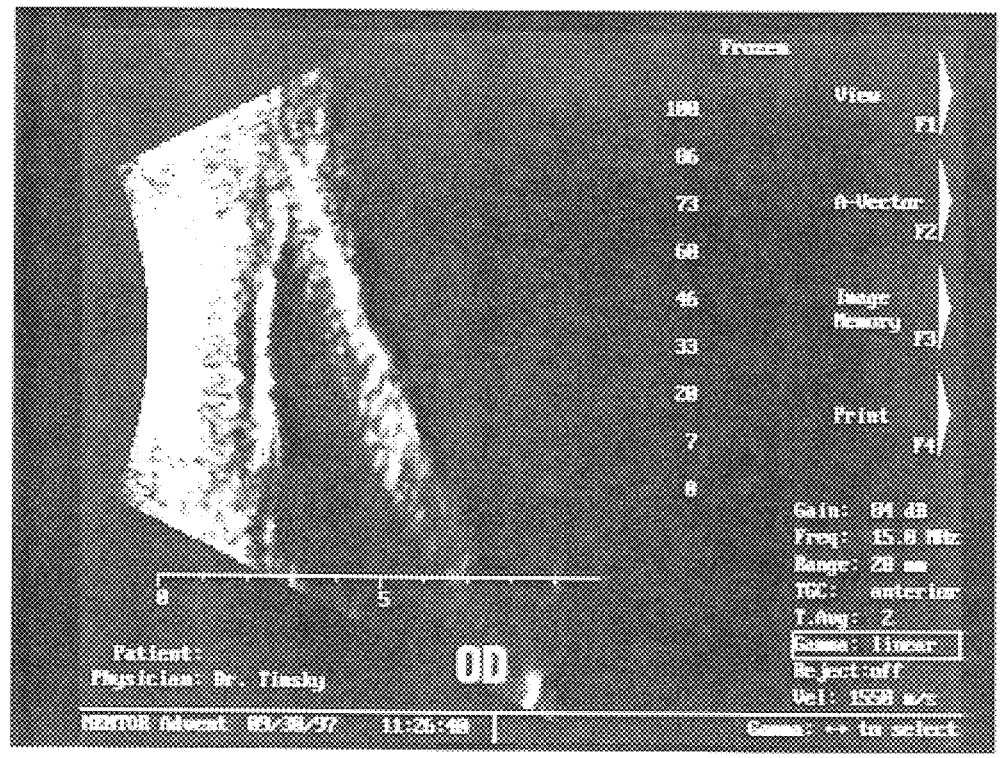
FIG. 31 is an anterior photograph of a cornea, iris, anterior chamber, and ciliary body created by selecting the linear gamma curve.
Figure 30:
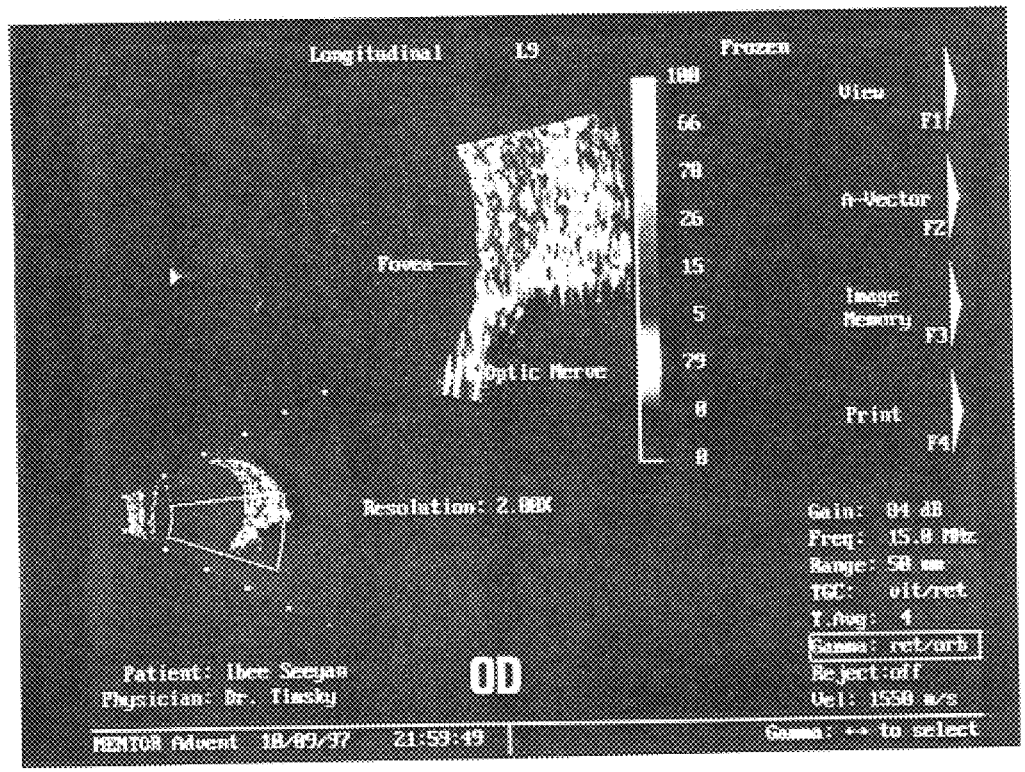
FIG. 30 is a window mode photograph of the same fovea created by selecting the "Retina/Orbit" gamma curve.
Figure 32:
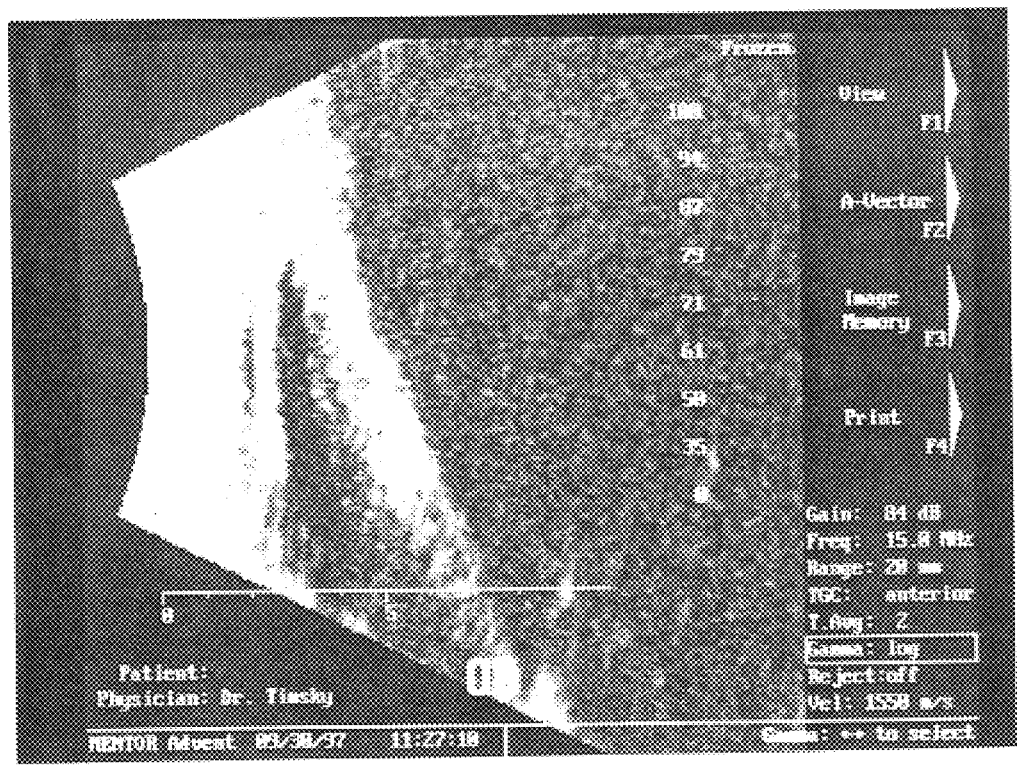
FIG. 32 is an anterior photograph of the same cornea, iris, anterior chamber, and ciliary body created by selecting the logarithmic gamma curve.
Figure 33:
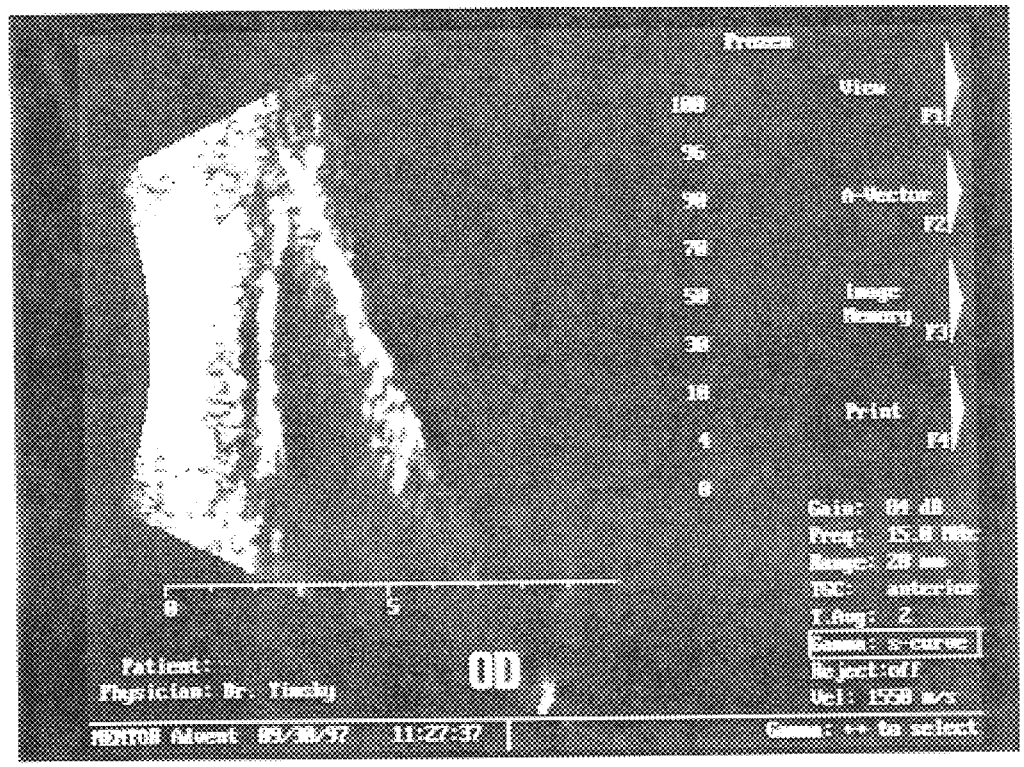
FIG. 33 is an anterior photograph of the same cornea, iris, anterior chamber, and ciliary body created by selecting the "S-Curve" gamma curve.
Figure 35:
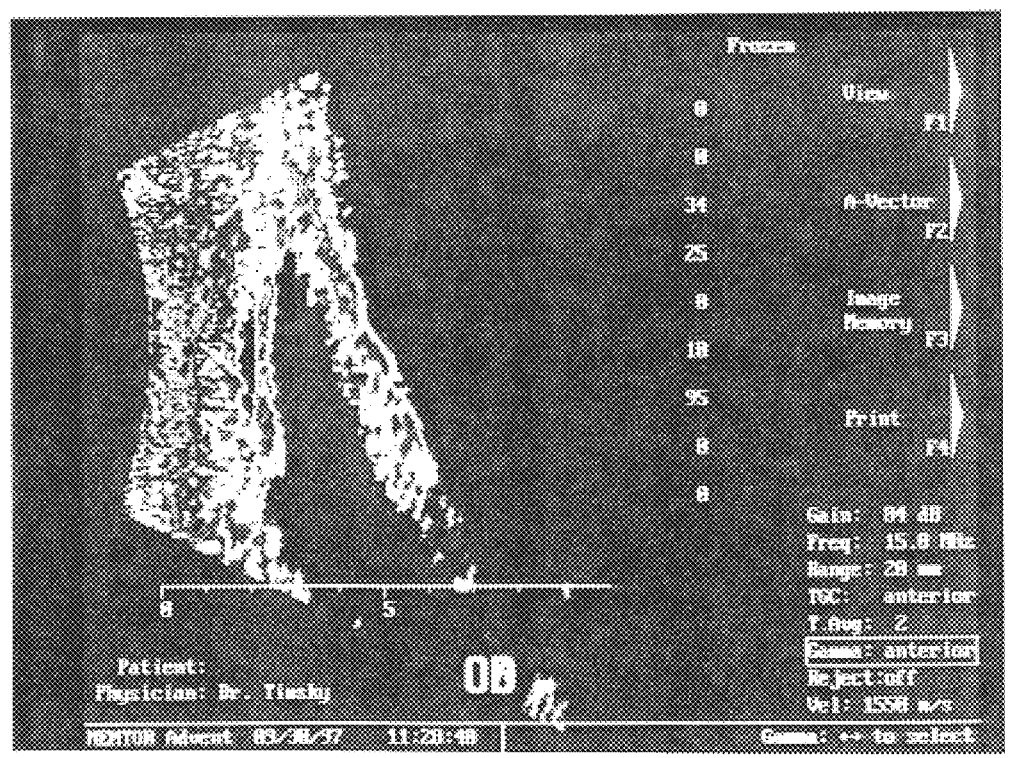
FIG. 35 is an anterior photograph of the same cornea, iris, anterior chamber, and ciliary body created by selecting the "Anterior" gamma curve.
Figure 34:
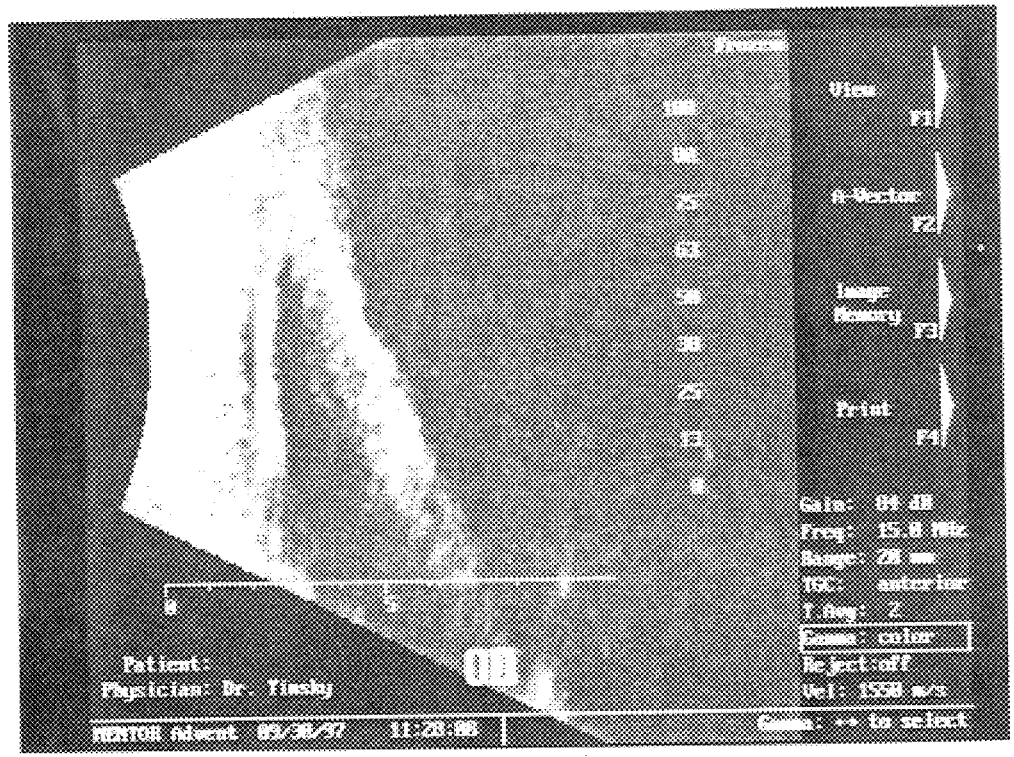
FIG. 34 is a black and white anterior photograph of the same cornea, iris, anterior chamber, and ciliary body created by selecting the multi-color gamma curve.
Figure 36:
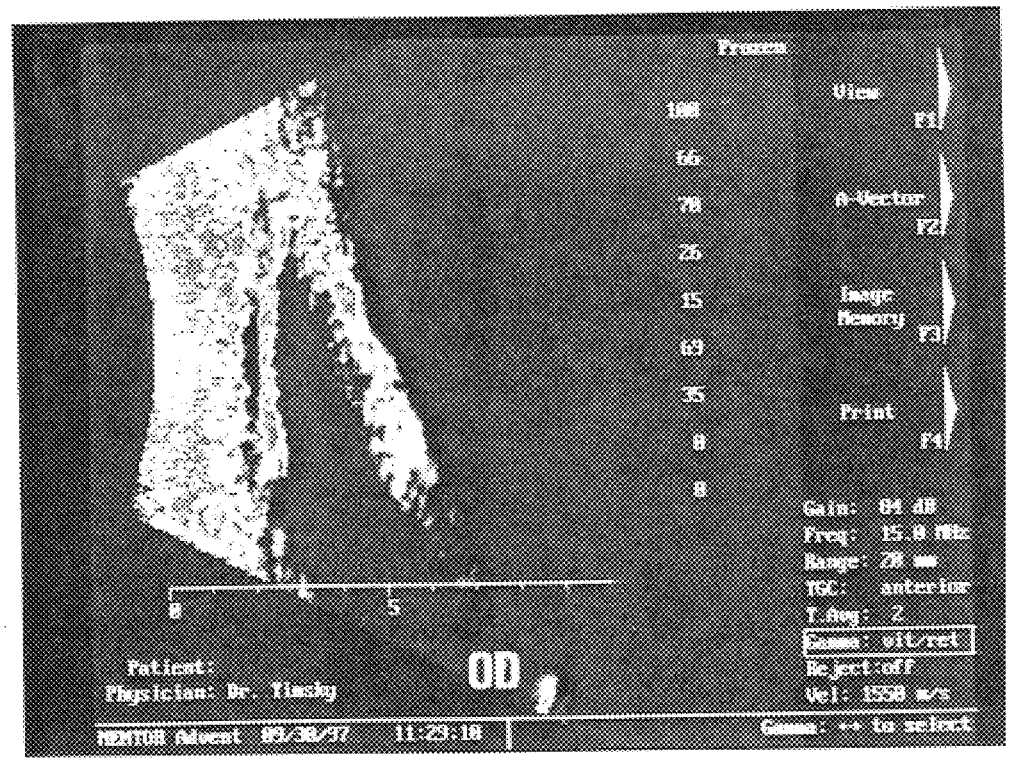
FIG. 36 is an anterior photograph of the same cornea, iris, anterior chamber, and ciliary body created by selecting the "Vitreous/Retina" gamma curve.
Figure 37:
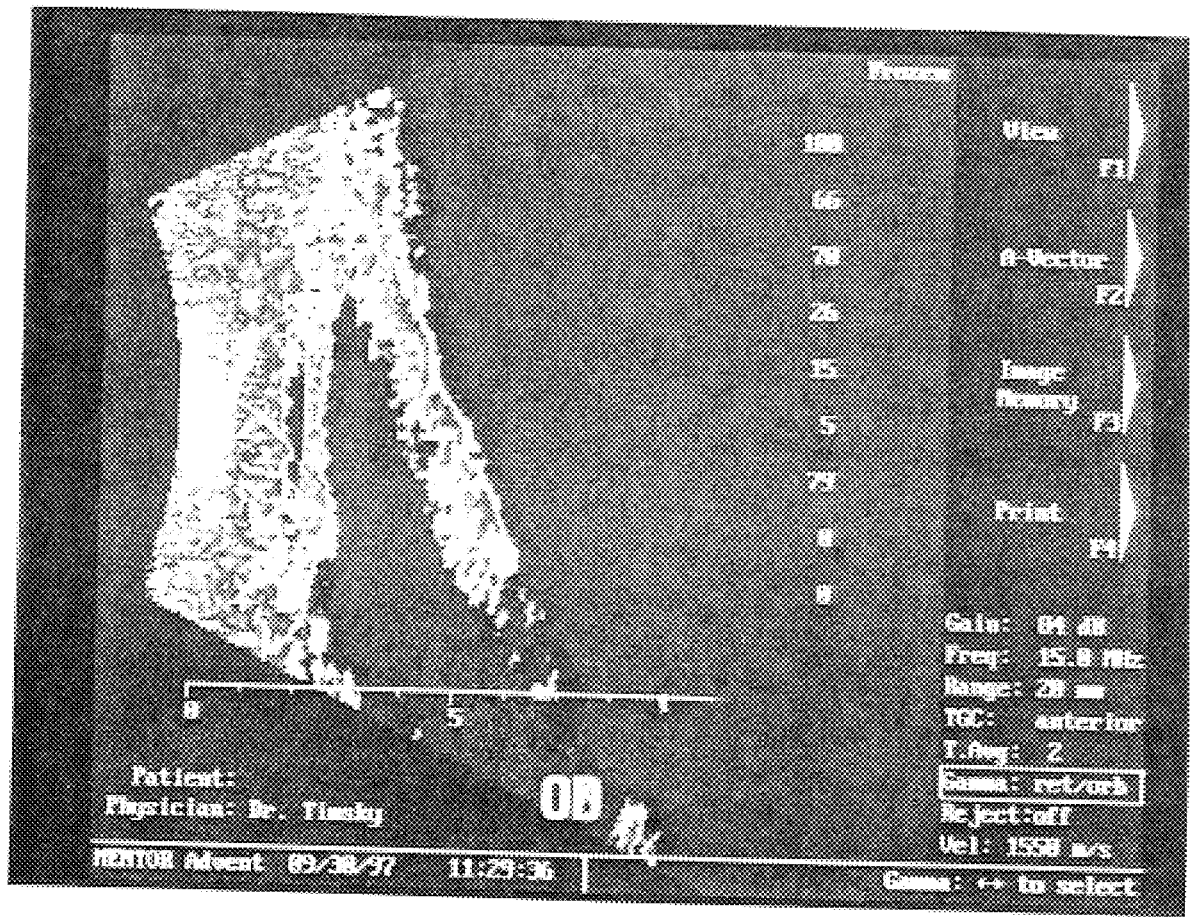
FIG. 37 is an anterior photograph of the same cornea, iris, anterior chamber, and ciliary body created by selecting the "Retina/Orbit" gamma curve.

FIG. 9 illustrates how the central processor causes the time persistence of an echo signal to be reflected in the image display. This feature is useful, for example, in searching for "floaters" in the vitreous fluid through the use of multiple sequential ultrasonic scans. The central processor initializes memory to hold information about each image point's previous echo signal intensity value and time persistence value (step 60). The time persistence value indicates the number of previous scans in which a particular image point has represented essentially the same echo signal intensity. After acquiring new electronic signals from the ultrasound transducer representing a new scan (step 62), the central processor updates each image point's echo signal intensity values and time persistence values in memory (step 63). The central processor compares the new echo signal intensity value with the previous one (step 64). If the echo signal intensities are the same, or within some threshold, the central processor increments that image point's time persistence value (step 66). If the echo signal intensities differ, the central processor sets the image point's time persistence value to zero and stores the new echo signal intensity value (step 68). The central processor then constructs data representing an image by coding each image point's new echo signal intensity with one of a plurality of color hues and by adjusting the color hue values to represent a brightness level that corresponds to the image point's time persistence value. For example, a physician searching for floaters, structures floating in the eye's vitreous, may place the ultrasound transducer near the patient's eye and continually scan the eye while the patient looks to the left and right. When the patient looks left and right, many eye structures remain stationary, however, the vitreous and structures within are stirred up much like the little snowflakes in a shaken souvenir snow-globe paperweight. The physician would see images where stationary objects gradually fade in brightness while the moving floaters track bright paths across the monitor. In another embodiment, the processor is programmed to cause moving objects to leave dim traces of their former position in subsequent images. In another embodiment, the central processor creates image data that codes time persistence information with color hue values and adjusts the color hue values to brighten the hues to correspond with echo signal intensity.

FIGS. 10–16 each show the gamma curves stored within the processing terminal. Graphs 10–12 and 14–16 plot brightness against echo signal intensity units. The solid lines represent the gamma curves in these graphs. Graph 13 plots the red, green, and blue values needed to produce a given color hue against echo signal intensity units.

Appendix A contains complete descriptions of each of the seven pre-defined gamma curves available to the user. Each description consists of a graph of the gamma function, any formulas used in its construction, and a tabular listing of the red, green, and blue values used to generate a particular color hue or shade of grey. The tables used for greyscale gamma curves have equal red, green, and blue values for each shade of grey in the curve.

| 1. | Linear | maps signal strength to brightness (monotonic). |
| 2. | Logarithmic | maps signal strength to brightness, highlighting weak signals (monotonic). |
| 3. | S Curve | maps signal strength to brightness, highlighting signals of average strength (monotonic). |
| 4. | Multi-color | maps signal strength to color, brightness is the same for all signal strengths. |
| 5. | Anterior | maps signal strength to a non-monotonic greyscale to highlight anterior segment pathology. |
| 6. | Vitreous/Retina | maps signal strength to a non-monotonic greyscale to highlight anterior segment pathology. |
| 7. | Retina/Orbit | maps signal strength to a non-monotonic greyscale to highlight retina or orbital segment pathology. |

FIGS. 17–23 each show a standard image of a retina, sclera, and orbital fat using each of the gamma curves provided. FIGS. 24–30 each show a window mode image of a fovea using each of the gamma curves provided. FIGS. 31–37 each show an anterior view image of a cornea, iris, and other eye structures using each of the gamma curves provided.

Figure 38:
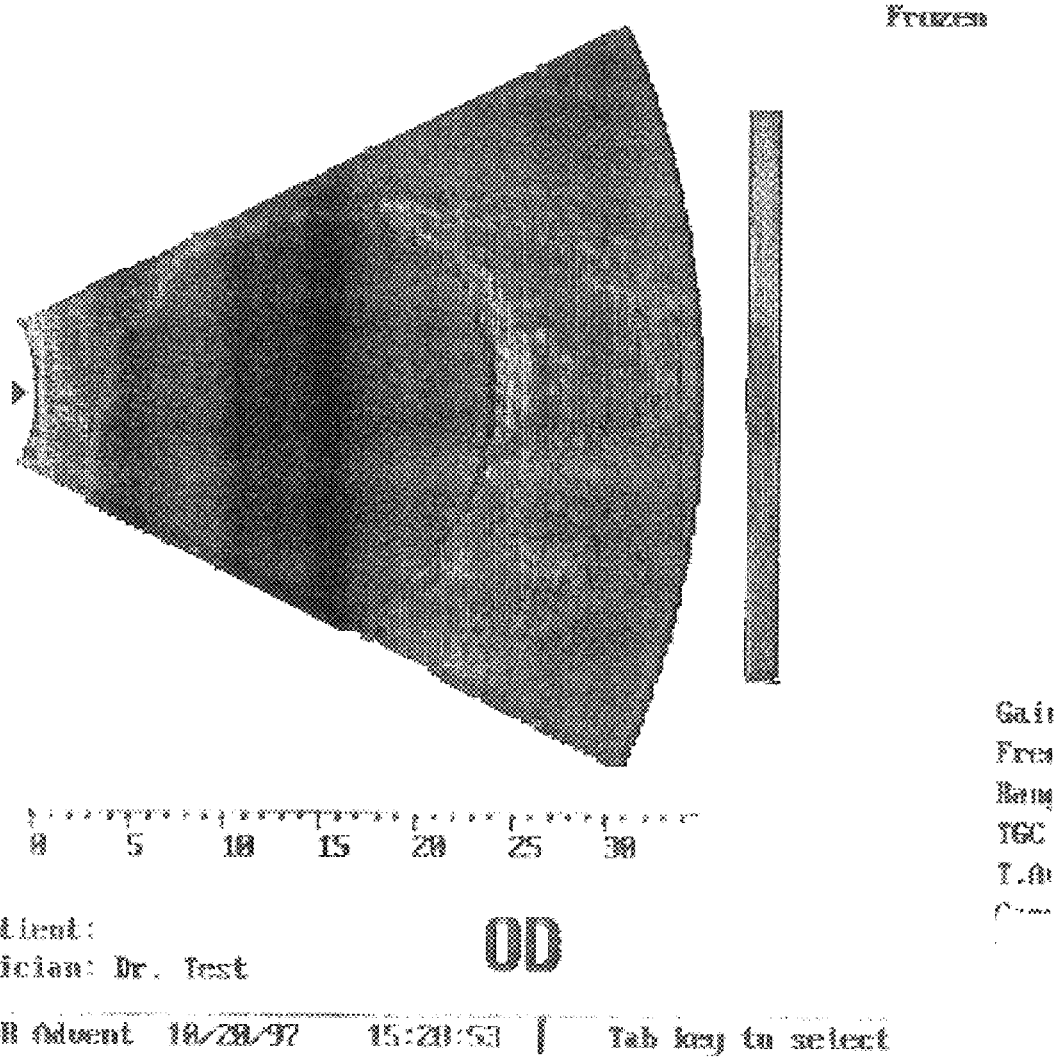
FIG. 38 is an eye image created by selecting the multi-color gamma curve.
Figure 39:
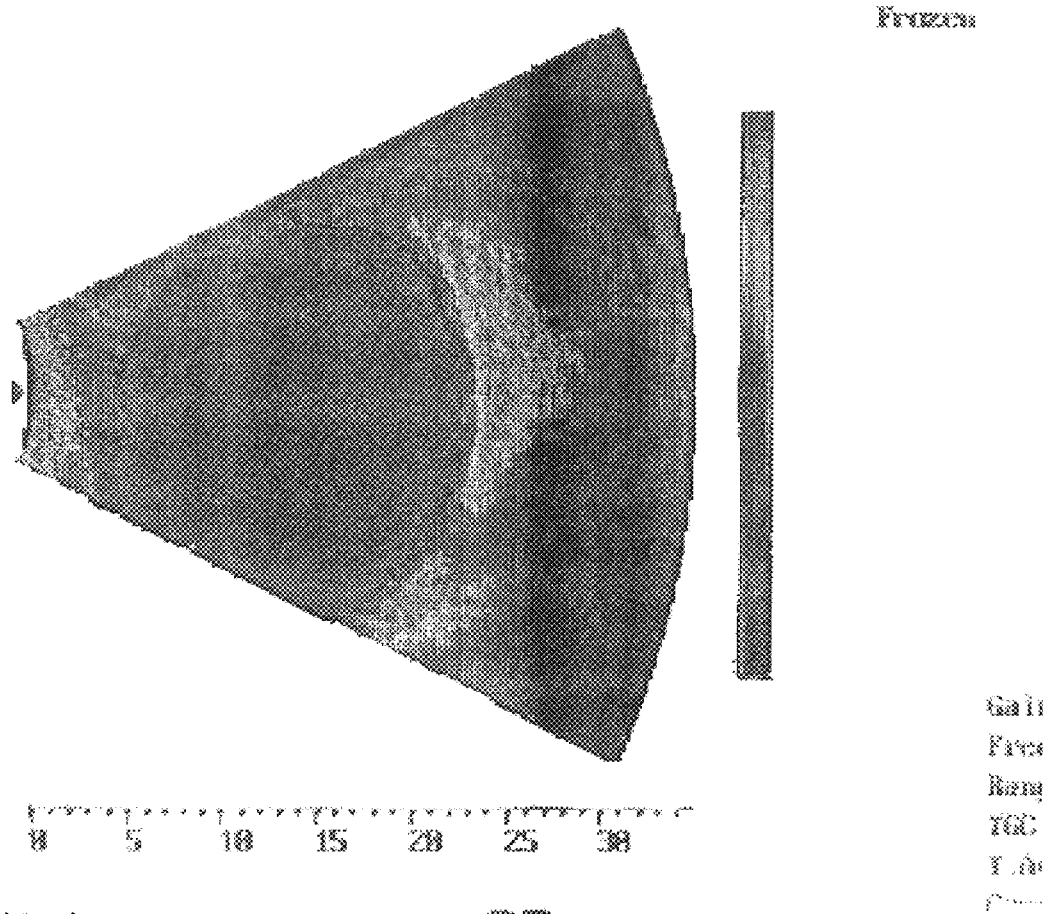
FIG. 39 is an image of the same eye created after a user has adjusted the gain knob to emphasize the boundary between the retina and sclera.

FIG. 38 is a color printout of an eye image created by using the multi-color gamma curve. Except for a few isolated patches of yellow hues, the image is almost entirely shades of blue and green. It is particularly difficult to visually distinguish the retina from the sclera at the green circle's right hand side. FIG. 39 is also a color printout of an eye image produced by the system, however, this image was produced after a user adjusted the gain knob. In this image, while the retina remained green, the sclera now appears as a noticeably different set of red hues. Color printouts of FIGS. 38 and 39 appear in appendix B.

With reference to FIG. 1, in operation of the system described above, a physician holds ultrasonic transducer 12 near patient's eye, and the image generated by processing terminal 16 appears on monitor 26. While the image may contain the information sought by the physician, human vision limitations may prevent the physician from seeing changes in structure impedances when slight changes are displayed with little visual contrast. For example, the differences in the echo signal intensities received by the ultrasound transducer 12 between layers of the retina may be so small as to make the many layers appear as one. However, by choosing the multi-color gamma curve, for example, and by adjusting gain knob 20, the physician can adjust the key echo signal intensities so they lie along a boundary between dramatically different gamma curve display characteristics and thus produce a display that shows the layers in high visual contrast, for example, with one layer of the retina in yellow and another in red, as opposed to both layers being displayed as closely similar hues of green.

The initial image may, additionally, show uninteresting features in high contrast. For example, an ophthalmologist checking the curvature of an iris for evidence of glaucoma may not care to see a highly contrasted display of fat globules behind the retina. By adjusting gain knob 20 and selecting an appropriate gamma curve, the physician can make the image portray the uninteresting structures in nearly the same color hue. To continue the example, the doctor examining an iris, after these adjustments, would no longer see highly contrasted fatty tissue behind the eye but instead, perhaps, closely similar blue hues.

The physician may instead choose to emphasize the appearance of some area of interest using one of the tailored non-monotonic monochromatic gamma curves or choose to emphasize structure boundaries by choosing an image that displays phase information.

If reverberation echo signals cloud the image, the physician might elect to have the system create an image color coding phase information, thereby creating an image where the reverberation echo signals are more easily distinguished from "genuine" echo signals.

If the physician wanted to examine structures trapped in the vitreous, the physician can view a continuous stream of ultrasound images that highlight moving structures within the eye by instructing the system to display time persistence information along with the echo signal intensity information. Thus, after the patient looks in different directions and returns to a fixed, predetermined eye position, structures that move appear differently than those that remain stationary.

There has been described novel and improved apparatus and techniques for producing ultrasound images of eye structures. It is evident that those skilled in the art may now make numerous uses and modifications of and departures from the specific embodiments described herein without departing from the claimed inventive concepts.

What is claimed is:

1. A system for producing visual representations of eye structures, the system comprising:

an ultrasonic transducer constructed and arranged to transmit ultrasound signals into eye structures, to receive ultrasound echo signals reflected by the eye structures, and to produce electronic signals representative of the received ultrasound echo signals;

a display device; and a processor electrically connected to the ultrasound transducer and the display device;

wherein the processor is constructed and arranged to receive the electronic signals from the ultrasonic transducer and to translate the electronic signals into data signals representing a non-background portion of an image of the eye structures for display on the display device by correlating each of a plurality of values of a parameter of the electronic signals with one of a plurality of different multichromatic color hues in accordance with a continuous gradation of the multichromatic color hues that forms the entirety of the non-background portion of the image.

2. A system in accordance with claim 1, wherein the processor uniformly correlates each other value of the parameter of the electronic signals with the background portion of the image.

3. A system in accordance with claim 2, wherein the background portion of the image is black.

4. A system in accordance with claim 1, wherein the eye structures comprise eyeball structures.

5. A system in accordance with claim 1, wherein the eye structures comprise tissue contained in an eye socket.

6. A system in accordance with claim 1, wherein the processor comprises pre-processor circuitry and a central processor.

7. A system in accordance with claim 1, wherein the display device comprises a printer.

8. A system in accordance with claim 1, wherein the display device comprises a video display.

9. A system in accordance with claim 1, further comprising a storage device connected to the display device and the processor, constructed and arranged to receive the data signals representing the multi-colored image and transmit the data signals to the display device at a delayed time.

10. A system in accordance with claim 9, wherein the storage device comprises a VCR.

11. A system in accordance with claim 9, wherein the storage device comprises computer-based storage.

12. A system in accordance with claim 1, wherein each color hue is represented by values of red, green, and blue.

13. A system in accordance with claim 1, wherein the processor is constructed and arranged to correlate the different values of the parameter of the electronic signals to the different multichromatic color hues using a lookup table that maps values to color hues.

14. A system in accordance with claim 13, wherein the lookup table is constructed and arranged to emphasize color contrast between structures in the eye anterior.

15. A system in accordance with claim 13, wherein the lookup table is constructed and arranged to emphasize color contrast between structures in the vitreous-retina area of the eye.

16. A system in accordance with claim 13, wherein the lookup table is constructed and arranged to emphasize color contrast between structures in the retina-orbit area of the eye.

17. A system in accordance with claim 1, wherein the display is constructed and arranged to display the image as an ultrasound B-Scan.

18. A system in accordance with claim 1, wherein the parameter comprises echo signal intensity.

19. A system in accordance with claim 1, further comprising a mechanism constructed and arranged to allow the user to adjust the correlation between each value of the parameter of the electronic signals and the different color hues.

20. A system in accordance with claim 19, wherein the mechanism is constructed and arranged to allow the adjustment of the correlation by a constant of proportionality.

21. A system for producing visual representations of eye structures, the system comprising:

an ultrasonic transducer constructed and arranged to transmit ultrasound signals into eye structures, to receive ultrasound echo signals reflected by the eye structures, and to produce electronic signals representative of the received ultrasound echo signals;

a display device; and a processor electrically connected to the ultrasound transducer and the display device;

wherein the processor is constructed and arranged to receive the electronic signals from the ultrasonic transducer and to translate the electronic signals into data signals representing an image of the eye structures for display on the display device by correlating different values of a parameter of the electronic signals with different values of a display characteristic in accordance with a gamma curve at least a portion of which is substantially continuous and non-monotonic.

22. A system in accordance with claim 21, wherein the display characteristic is monochromatic brightness.

23. A system in accordance with claim 21, wherein the display characteristic is color hue.

24. A system in accordance with claim 21, further comprising a mechanism constructed and arranged to allow the user to adjust the correlation between each value of the parameter of the electronic signals and the different values of the display characteristic.

25. A system in accordance with claim 24, wherein the mechanism is constructed and arranged to allow adjustment of the correlation by a constant of proportionality.

26. A system for producing visual representations of eye structures, the system comprising:

an ultrasonic transducer constructed and arranged to transmit ultrasound signals into eye structures, to receive ultrasound echo signals reflected by the eye structures, and to produce electronic signals representative of the received ultrasound echo signals;

a display device; and a processor electrically connected to the ultrasound transducer and the display device;

wherein the processor is constructed and arranged to receive the electronic signals from an ultrasonic transducer and to translate the electronic signals into data signals representing a multi-colored image for display on the display device by correlating different values of a first parameter of the electronic signals with different colors and by correlating different values of a second parameter of the same electronic signals with different degrees of color brightness.

27. A system in accordance with claim 26, wherein the first parameter comprises phase information and the second parameter comprises echo signal intensity.

28. A system in accordance with claim 26, wherein the first parameter comprises echo signal intensity and the second parameter comprises phase information.

29. A system in accordance with claim 26, wherein the first parameter comprises time persistence and the second parameter comprises echo signal intensity.

30. A system in accordance with claim 26, wherein the first parameter comprises echo signal intensity and the second parameter comprises time persistence.

31. A system for producing visual representations of eye structures, the system comprising:

an ultrasonic transducer constructed to transmit ultrasound signals into eye structures, to receive ultrasound echo signals reflected by the eye structures, and to produce electronic signals representative of the received ultrasound echo signals;

a display device; and a processor electrically connected to the ultrasound transducer and the display device;

wherein the processor is constructed and arranged to receive the electronic signals from an ultrasonic transducer and to translate the electronic signals into data signals representing an image of the eye structures for display on the display device, the translation comprising processing of phase information of the electronic signals.

32. A system in accordance with claim 31, wherein the processing of phase information of the electronic signals comprises determining whether the electronic signals represent a location of a rise in impedance or a drop in impedance.

33. A system in accordance with claim 32, wherein the processor is further constructed and arranged to cause the location to be displayed in one color hue for a rise in impedance and another color hue for a drop in impedance.

34. A system for producing visual representations of eye structures, the system comprising:

an ultrasonic transducer constructed to transmit ultrasound signals into eye structures, to receive ultrasound echo signals reflected by the eye structures, and to produce electronic signals representative of the received ultrasound echo signals;

a display device; and a processor electrically connected to the ultrasound transducer and the display device;

wherein the processor is constructed and arranged to receive the electronic signals from an ultrasonic transducer and to translate the electronic signals into data signals representing an image of the eye structures for display on the display device by correlating different values of a first parameter of the electronic signals with different values of first display characteristics and different values of a second, time persistence parameter of the electronic signals, with different values of second display characteristics.

35. A system in accordance with claim 34, wherein the translation of the electronic signals into data signals representing an image comprises correlating different values of time persistence information with different color hues and correlating brightness of the color hues with different values of echo signal intensity.

36. A system in accordance with claim 34, wherein the translation of the electronic signals into data signals representing an image comprises correlating different values of echo signal intensity with different color hues and correlating brightness of the color hues with different values of time persistence.

\* \* \* \* \*